(12) United States Patent
Kodgule et al.

(10) Patent No.: US 10,376,649 B2
(45) Date of Patent: Aug. 13, 2019

(54) DRUG DELIVERY DEVICE FOR DELIVERY OF TWO OR MORE INDEPENDENTLY USER SELECTABLE MULTIPLE DOSES OF MEDICAMENTS WITH USER OPERABLE VARIABLE DOSE LOCKING MECHANISMS

(71) Applicant: Wockhardt Limited, Aurangabad (IN)

(72) Inventors: Mandar Kodgule, Mumbai (IN); Sachidananda Yallambalsi, Bangalore (IN); Umesh Joshi, Aurangabad (IN); Sanjib De, Burdwan (IN)

(73) Assignee: WOCKHARDT LIMITED, Chikalthana, Aurangabad (IN)

( * ) Notice: Subject to any disclaimer, the term of this patent is extended or adjusted under 35 U.S.C. 154(b) by 120 days.

(21) Appl. No.: 15/523,363

(22) PCT Filed: Oct. 26, 2015

(86) PCT No.: PCT/IB2015/058237
§ 371 (c)(1),
(2) Date: Apr. 28, 2017

(87) PCT Pub. No.: WO2016/067179
PCT Pub. Date: May 6, 2016

(65) Prior Publication Data
US 2017/0239422 A1    Aug. 24, 2017

(30) Foreign Application Priority Data

Oct. 29, 2014 (IN) .................. 3426/MUM/2014

(51) Int. Cl.
*A61M 5/00* (2006.01)
*A61M 5/315* (2006.01)
(Continued)

(52) U.S. Cl.
CPC .......... *A61M 5/31536* (2013.01); *A61M 5/19* (2013.01); *A61M 5/20* (2013.01);
(Continued)

(58) Field of Classification Search
CPC ................. A61M 5/19; A61M 5/2448; A61M 2005/1787; A61M 5/2066
See application file for complete search history.

(56) References Cited

U.S. PATENT DOCUMENTS 5,253,785 A * 10/1993 Haber ................ A61M 5/19
222/135
5,378,233 A * 1/1995 Haber ................ A61M 5/19
604/135

(Continued)

*Primary Examiner* — William R Carpenter
(74) *Attorney, Agent, or Firm* — Bio Intellectual Property Services LLC (Bio IPS); O. (Sam) Zaghmout

(57) ABSTRACT

It may be one of the aspects of the invention that a drug delivery device for delivery of two or more independently user selectable multiple doses of medicaments contained in separate cartridges of the medicament reservoirs within a single device operatively connected to a single dispense interface which may be operatively connected to a single activation button; It may be another aspect of the invention that unlocking of the user operable variable dose locking mechanism of the drug delivery device may be easily carried out by one hand operation by a lock slider unlock by the user.

9 Claims, 19 Drawing Sheets

(51) Int. Cl.
*A61M 5/19* (2006.01)
*A61M 5/20* (2006.01)
*A61M 5/28* (2006.01)

(52) U.S. Cl.
CPC .......... *A61M 5/28* (2013.01); *A61M 5/31535* (2013.01); *A61M 5/31596* (2013.01); *A61M 2005/2073* (2013.01)

(56) References Cited

U.S. PATENT DOCUMENTS

| | | | | |
|---|---|---|---|---|
| 5,478,323 | A * | 12/1995 | Westwood | A61M 5/19 604/191 |
| 5,584,815 | A * | 12/1996 | Pawelka | A61M 5/19 604/135 |
| 6,673,049 | B2 * | 1/2004 | Hommann | A61M 5/24 604/187 |
| 9,220,846 | B2 * | 12/2015 | Jones | A61M 5/31545 |
| 9,333,302 | B2 * | 5/2016 | De Sausmarez Lintell | ................ A61M 5/19 |
| 2013/0253465 | A1 * | 9/2013 | Holtwick | A61M 5/19 604/411 |

* cited by examiner

DRUG DELIVERY DEVICE FOR DELIVERY OF TWO OR MORE INDEPENDENTLY USER SELECTABLE MULTIPLE DOSES OF MEDICAMENTS WITH USER OPERABLE VARIABLE DOSE LOCKING MECHANISMS

FIELD OF INVENTION

It may be one of the aspects of the invention that a drug delivery device for delivery of two or more independently user selectable multiple doses of medicaments contained in separate cartridges of the medicament reservoirs within a single device operatively connected to a single dispense interface which may be operatively connected to a single activation button; the device further may comprise two or more separate independent dose setters of the dose setting mechanisms contained within the housings, wherein the device may comprise user operable variable dose locking mechanisms operably connected to each of the dose setters which allow the selection of the appropriate doses on unlocking the user operable variable dose locking mechanism. Activation of single activation button dispenses the selected doses of two or more medicaments and on completion of the doses deliveries user operable variable dose locking mechanism automatically gets locked. It may be another aspect of the invention that unlocking of the user operable variable dose locking mechanism of the drug delivery device may be easily carried out by one hand operation by a lock slider unlock by the user.

BACKGROUND OF THE INVENTION

Treatment of certain diseases requires use of one or more different active medicaments. Optimum therapeutic doses of these different active medicaments may have to be delivered in a specific relationship with each other. A single formulation of these different active medicaments may not be possible for reasons such as stability, toxicology and ineffective therapeutic performance.

Delivery related problems of different active medicaments when delivering one or more active medicaments includes interaction with each other during the long-term, shelf life storage of the formulation. Hence the preferred method of delivery involves storing one or more active medicaments separately and combining them at the point of delivery by the various known delivery mechanisms such as inhalation route, pumps, needle-less injection and injection.

A further problem in the multi medicament combination therapy is that quantities and/or proportions of one or more active medicaments may vary for each user and also may vary at different stages of therapy. Other possible variations in the combination therapy of one or more active medicaments are variation in doses in response to a patient's symptoms or physical condition. Hence in such cases pre-mixed formulations of multiple active medicaments may prove to be ineffective as these pre-mixed formulations would have a fixed ratio of different active medicaments.

Use of more than one drug delivery device for delivery of one or more medicaments calls for additional patient skills such as dexterity, computational competency etc. Besides the economic factor other associated problems may be in terms of handling multi devices especially when the patient is on high mobility and storage of more than one drug delivery device.

Hence the need for delivery of one or more active medicaments may be accomplished by devices and methods by a single injection or delivery step that is simple for the user to perform.

Prior art patents U.S. Pat. Nos. 8,092,421, 8,092,422 and 8,376,987 related to delivery of one or more active medicaments comprise two chamber syringes or carpule. Though chamber syringes of these prior arts may be able to hold one or medicaments they are unsuitable for use with an injection pen device. U.S. Pat. No. 8,651,338 patent relates to a delivery device for delivery of predefined combination of one or more medicaments comprising a user settable variable dose and a fixed dose wherein the user may be able to set the variable doses of one of the medicaments and the medicament may be dispensed through a single activation single dispense interface. In the invention of US '338 the fixed dosage of the drug is automatically set based on the setting of the variable dose. US'338 invention allows varying quantity of one of both medicaments; however varying "fixed" dose medicament may be achieved by manufacturing a variety of "fixed dose" medicament containing packages with each variant containing a different volume and/or concentration of the "fixed dose" medicament. US'338 invention is disadvantageous as it requires carrying several packages of different volume and/or concentration of the "fixed dose" medicament to meet the variable dose delivery requirements of the "fixed dose"; similarly prior art patent applications US20130261556, US20130245561, WO2012085173 and US20130197447 have the features of US'338 with regard to delivery of predefined combination of one or more medicaments.

The prior art patent application US20130245604 delivery device comprises two chambers to deliver three or more medicaments by a single variable dose setting through a single interface by a single activation. In this device the dosage of second medicament is chosen from an electromechanical dose setting mechanism from a programmed stored therapeutic dose profiles; the stored therapeutic dose profiles may be a linear dose profile; a non-linear dose profile; a fixed ratio-fixed dose profile; a fixed dose-variable dose profile; a delayed fixed dose-variable dose profile; or a multi-level, a fixed dose variable dose profile. The delivery device of US'604 is disadvantageous as use of any one or more combination of second medicament stored therapeutic dose profile would not be as flexible as a variable dose profile matching the wide variety of patient profile populace.

WO2012107493 relates to a delivery device for delivery of user settable variable doses of first medicament and preset doses of second medicament through either a single dispense interface wherein activation of the second medicament delivery system locks out the first dose delivery mechanism preventing further dose setting and administration of the first medicament.

WO1994003392 is directed to a variable proportion dispenser, especially useful for dispensing different types of insulin in amounts and proportions selected by the user. Once the combined dosage is selected, both in amount and proportion, the same proportion combined dosage will be automatically delivered for each actuation cycle of the dispenser. However the device disclosed in WO '392 does not permit the user to adjust both the quantity and proportion of the two medicament components to be delivered by the dispenser at will, but allows doing so by modification/replacement of certain components of the device etc. This calls for additional skill requirement and training for the patient in effecting modification in the device. Hence the use of WO'392 device has a limited scope for meeting the diverse variable doses of one or more medicaments and would fall short of full flexibility as per the patient's requirement. Further disadvantage of this device is that when only one medicament i.e. one type of insulin to be delivered, the second medicament may be accidentally set.

The prior art patent applications US20120220949, US20120130346, US20120136334, US20120226238, US20120123346, US20120116349, US20130144262, US201302-18089, US20130226081, US20130226143, US20130245563, EP2514455, EP2514-457, EP2514450, EP2514459, WO2012072562, WO2012143434 and WO2012-143435 are related to medicated module attachable to a drug delivery device each of which signifies a specified medicated module feature. The medicament in these medicated modules would be analogous to fixed doses which are non user settable ones as in US'338.

Hence there is a greater need for providing drug delivery devices and methods for the delivery of two or more medicaments in varying quantities as per the patient's requirement in a single injection or delivery step that is easier for the user to perform. In specific embodiments, the present invention overcomes the problem by providing separate storage containers for two or more medicaments with individual user operable dose locking mechanisms which enable dose setting by individual dose setters in the unlocked condition and gets locked on completion of the dose delivery. The patient or the healthcare professional would find the use of the drug delivery device easy.

The problem addressed by the present invention is to provide a drug delivery device and a method of its use wherein it facilitates administration of (i) two or more medicaments in varying quantities as per the patient's dosage requirement and (ii) three or more medicaments where in two of medicaments may be in varying quantities and third medicament may be in fixed quantity as per the patient's dosage requirement.

SUMMARY OF THE INVENTION

It may be one of the aspects of the invention that a drug delivery device for delivery of two or more independently user selectable multiple doses of medicaments contained in separate cartridges of the medicament reservoirs within a single device operatively connected to a single dispense interface which may be operatively connected to a single activation button; the device further may comprise two or more separate independent dose setters of the dose setting mechanisms contained within the housings, wherein the device may comprise user operable variable dose locking mechanisms operably connected to each of the dose setters which allow the selection of the appropriate doses on unlocking the user operable variable dose locking mechanism. Activation of single activation button dispenses the selected doses of two or more medicaments and on completion of the doses deliveries user operable variable dose locking mechanism automatically gets locked.

It may be another aspect of the invention that the user operable variable dose locking mechanism of the drug delivery device of the invention may be easier to operate i.e. unlocking the locking mechanism for setting the dose by the user in general and infirm and old people in particular.

It may be another aspect of the invention that unlocking of the user operable variable dose locking mechanism of the drug delivery device may be easily carried out by one hand operation by a lock slider unlock by the user.

It may be another aspect of the invention that the user operable variable dose locking mechanisms in an embodiment of the drug delivery device allows delivery of even two equal or unequal variable doses of the of the first medicament (1*aa*) and the second medicament (11*aa*) by a single activation through a single interface and automatically locks the two dose setting mechanisms on completion of the medicament dosages.

It may be another aspect of the invention that the user operable variable dose locking mechanisms in an embodiment of the drug delivery device allow delivery of even two equal or unequal variable doses and one fixed dose of the of the first medicament (1*aa*), second medicament (11*aa*) and third medicament (111*aa*) by a single activation through a single interface and automatically locks the two dose setting mechanisms on completion of the medicament dosages.

The drug delivery device of the present invention, a multiple dose, user selectable one, in specific embodiments may deliver two or more independently user selectable medicaments within a single device through a single dispense interface. The medicaments i.e. the first medicament (1*aa*) and the second medicament (11*aa*) may be delivered through a common needle hub through a single needle. The drug delivery device in one of the embodiments may comprise two separate independent dose setters for each of the two medicaments, wherein each dose setter of the dose setting mechanism with an independent user operable variable dose locking mechanism operably connected thereto, may facilitate the selection of the appropriate dose on unlocking the dose locking mechanism. It may be another aspect of the invention that the dose locking mechanisms may be operatively connected to dose drums of the dose setting mechanisms. The medicaments may be contained in cartridges which are contained in medicament reservoirs.

A drug delivery device adapted to deliver two or more medicaments comprising two or more housings; each housing comprising a dose setting mechanism, a dose delivery mechanism and a removable medicament cartridge. The device (12) comprising a common needle hub, a dispensing interface and an activation mechanism. The device is characterized in that (i) it comprises a user operable dose locking mechanism capable of locking and unlocking the dose setting mechanism and dose delivery mechanism; and (ii) the device is capable of delivering at least one medicament in a variable dose.

The drug delivery device is adapted to deliver three medicaments such that two medicaments are delivered as variable doses and one medicament is delivered as a fixed dose.

The drug delivery device is adapted to deliver two medicaments comprising two housings wherein one medicament is delivered as variable dose and one medicament as fixed dose.

The drug delivery device is adapted to deliver two medicaments comprising two housings wherein two medicaments are delivered as variable doses.

The drug delivery device is adapted to deliver at least one medicament in a fixed dose.

The drug delivery device user operable dose locking mechanism is adapted to set a variable or fixed dose.

In an embodiment of the drug delivery device of the invention one or more medicaments are selected from group comprising human insulin, a human insulin analogue, a human insulin derivative, exendin-3, exendin-4, an exendin-3 analogue, an exendin-4 analogue, an exendin-3 derivative or an exendin-4 derivative, glucagon-like peptide-1 (GLP-1), a GLP-1 analogue, a GLP-1 derivative, Sedatives, Hypnotics, Anti-inflammatory agents, Antibiotics, Antidiabetics, Antihypertensives, Anti-Osteoporosis Agents, Antithrombotic Agents, Antivirals, Antifungals, Anticholinergic Agents, Anxiolytic Agents, Adrenergics, Antipsychotics, Anti-Parkinsonism Agents, Anticonvulsants, CNS Stimulants, Antianginal Agents, Antiarrhythmics, Antihyperlipidemic Drugs, Diuretics, Antiasthmatics, Anticoagulants, Antianemia Agents, Vitamins, Hormones, Antihistaminics, Anticancer Agents, Antiallergics, Antiarthritis Agents, Antialzheimers' Agents, Vasopressin Antagonists, Anticonvulsants, Steroids, Anesthetics, Thrombolytics, Antacids, Proton Pump Inhibitors, Protease Inhibitors, Platelet Aggregation Inhibitors, Mucolytics, Antimalarials, Antiemetics, Laxatives, Expectorants, Enzymes, Contraceptives, Bronchodilators, Antitussives, Antimigraine Agents, Anthelmintics, Anorexiants, and Antiepileptics and combination thereof.

Examples of insulin analogue without limitation, Gly (A21), Arg(B31), Arg(B32) human insulin; Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin or combination thereof.

Examples of derivatives of human insulin are threonine methyl ester$^{830}$ human insulin and $N^{\epsilon B29}$-tetradecanoyl des (B30) human insulin.

Examples of Exendin-4 selected from the group comprising exendin-4(1-39), a peptide with the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-P-ro-Pro-Ser-NH$_2$ or mixture thereof.

In an embodiment of the drug delivery device of the invention one of the medicaments selected from the group comprising, GLP-1(7-37), insulinotropic analogue thereof and insulinotropic derivatives thereof. Non-limiting examples of GLP-1 analogues are GLP-1(7-36) amide, Arg$^{34}$-GLP-1(7-37), Gly$^8$-GLP-1(7-37), Gly$^8$-GLP-1 (7-36)-amide, Aib$^8$-GLP-1 (7-36)-amide, Aib$^8$-GLP-1 (7-37), Val$^8$Asp$^{22}$-GLP-1 (7-36)-amide, Val$^8$-GLP-1(7-36)-amide, Val$^8$Asp$^{22}$-GLP-1 (7-37), and Val$^8$Asp$^{22}$-GLP-1(7-37). Non-limiting examples of GLP-1 derivatives are desamino-His$^7$, Arg$^{26}$, Lys$^{34}$ (N$^\gamma$-(γ-Glu(Nα-hexadecanoyl)))-GLP-1(7-37), desamino-His$^7$, Arg$^{26}$, Lys$^{34}$(N$^\gamma$-octanoyl)-GLP-1(7-37), Arg$^{26,34}$, Lys$^{33}$(N$^\gamma$-(ω-carboxypentadecanoyl))-GLP-1(7-38), Arg$^{26,34}$, Lys$^{36}$(N$^\gamma$-(γ-Glu(Nα.-hexadecanoyl)))-GLP-1(7-36) and Arg$^{34}$, Lys$^{26}$ (N$^\gamma$-(γ-Glu(Nα-hexadecanoyl)))-GLP-1(7-37), Val$^8$Glu$^{22}$-GLP-1 (7-36)-amide, Val$^8$Glu$^{22}$-GLP-1 (7-37), Val$^8$Lys$^{22}$-GLP-1 (7-36)-amide, Val$^8$Lys$^{22}$-GLP-1 (7-37), Val$^8$Arg$^{22}$-GLP-1 (7-36)-amide, Val8Arg$^{22}$-GLP-1 (7-37), Val$^8$His$^{22}$-GLP-1 (7-36)-amide, Val$^8$His$^{22}$-GLP-1(7-37), Val$^8$Trp$^{19}$Glu$^{22}$-GLP-1 (7-37), Val$^8$Glu$^{22}$Val$^{25}$-GLP-1 (7-37), Val$^8$Tyr$^{16}$Glu$^{22}$-GLP-1 (7-37), Val$^8$Trp$^{16}$Glu$^{22}$-GLP-1 (7-37), Val$^8$Leu$^{16}$Glu$^{22}$-GLP-1 (7-37), Val$^8$Tyr$^{18}$Glu$^{22}$-GLP-1 (7-37), Val$^8$Glu$^{22}$His$^{37}$-GLP-1 (7-37), Val$^8$Glu$^{22}$Ile$^{33}$-GLP-1 (7-37), Val$^8$Trp$^{16}$Glu$^{22}$Val$^{25}$Ile$^{33}$-GLP-1 (7-37), Val$^8$Trp$^{16}$Glu$^{22}$Ile$^{33}$-GLP-1 (7-37), Val$^8$Glu$^{22}$Val$^{25}$Ile$^{33}$-GLP-1 (7-37), Val$^8$Trp$^{16}$Glu$^{22}$Val$^{25}$-GLP-1 (7-37), and analogues thereof.

Non-limiting examples of suitable therapeutically active pharmaceutical ingredient may also comprise 6-Methylmercaptopurine (MMPR), Abciximab, Acetaminophen, Acetazolamide Sodium, Acetylcysteine, ACTH, Acyclovir Sodium, Adenosine, Alatrofloxacin Mesylate, Albumin, Serum Human, Alcohol, Ethyl, Aldesleukin, Alemtuzumab, Alfentanil HCl, Allopurinol Sodium, Alprostadil, Alteplase, Amifostine, Amikacin Sulfate, Amino Acids Solution, Aminocaproic Acid, Aminophylline, Aminosyn 3.5 M, Aminosyn 7, Aminosyn 8.5, Aminosyn II, Amiodarone HCl, Ammonium Chloride, Amobarbital Sodium, Amoxicillin Sodium, Amoxicillin-Clavulanate, Amphotericin B, Amphotericin B Cholesteryl Sulfate Complex, Amphotericin B Lipid Complex, Amphotericin B Liposome, Ampicillin Sodium, Ampicillin Sodium, Sulbactam Sodium, Amsacrine, Anakinra, Anidulafungin, Anileridine Phosphate, Anistreplase, Anti-Thymocyte Globulin (Rabbit), Argatroban, Arginine HCl, Aripiprazole, Ascorbic Acid, Asparaginase, Atenolol, Atracurium Besylate, Atropine Sulfate, Aurothioglucose, Azacitidine, Azathioprine Sodium, Azithromycin Dihydrate, Azlocillin Sodium, Aztreonam, Bacitracin, Baclofen, Benzquinamide HCl, Benztropine Mesylate, Betamethasone Sodium Phosphate, Bevacizumab, Bivalirudin, Bleomycin Sulfate, Blood, Whole, Bortezomib, Bretylium Tosylate, Brompheniramine Maleate, Bumetanide, Bupivacaine HCl, Bupivacaine Liposome, Buprenorphine HCl, Busulfan, Butorphanol Tartrate, Caffeine, Caffeine Citrate, Calcitriol, Calcium Chloride, Calcium Disodium Edetate, Calcium Gluceptate, Calcium Gluconate, Carbenicillin Disodium, Carboplatin, Carmustine, Caspofungin Acetate, Cefamandole Nafate, Cefazedon, Cefazolin Sodium, Cefepime HCl, Cefmenoxime, Cefmetazole Sodium, Cefonicid Sodium, Cefoperazone Sodium, Ceforanide, Cefotaxime Sodium, Cefotetan Disodium, Cefoxitin Sodium, Cefpirome Sulfate, Ceftaroline Fosamil, Ceftazidime, Ceftizoxime Sodium, Ceftriaxone Sodium, Cefuroxime Sodium, Cephalothin Sodium, Cephalothin Sodium, Neutral, Cephapirin Sodium, Cephradine, Cetuximab, Chloramphenicol Sodium Succinate, Chlordiazepoxide HCl, Chlormethiazole Edisylate, Chloroquine Sulfate, Chlorothiazide Sodium, Chlorpheniramine Maleate, Chlorpromazine HCl, Cidofovir, Cimetidine HCl, Ciprofloxacin, Cisatracurium Besylate, Cisplatin, Cladribine, Clarithromycin, Clindamycin Phosphate, Clinimix Injections, Clofarabine, Clonazepam, Clonidine HCl, Cloxacillin Sodium, Codeine Phosphate, Codeine Sulfate, Colistimethate Sodium, Collagen (For Embolization), Conivaptan HCl, Conjugated Estrogens, Corticotropin, Co-Trimoxazole, Cyanocobalamin, Cyclizine Lactate, Cyclophosphamide, Cyclosporine, Cytarabine, Dacarbazine, Dactinomycin, Dalteparin Sodium, Danaparoid Sodium, Dantrolene Sodium, Daptomycin, Daunorubicin HCl, Deferoxamine Mesylate, Deslanoside, Dexamethasone Sodium Phosphate, Dexamethasone Sodium Succinate, Dexmedetomidine HCl, Dexrazoxane, Dextran, Diamorphine HCl, Diatrizoate (Sodium And Meglumine), Diazepam, Diazoxide, Dichloromethotrexate, Diethylstilbestrol Diphosphate, Digitoxin, Digoxin, Dihydroergotamine Mesylate, Diltiazem HCl, Dimenhydrinate, Diphenhydramine HCl, Disopyramide Phosphate, Disulfiram, Dobutamine HCl, Docetaxel, Dolasetron Mesylate, Dopamine HCl, Doripenem, Doxacurium Chloride, Doxapram HCl, Doxorubicin HCl, Doxorubicin HCl Liposome, Doxycycline Hyclate, Droperidol, Drotrecogin Alfa, Edetate Calcium Disodium, Edrophonium Chloride, Enalaprilat, Enoxaparin Sodium, Ephedrine Sulfate, Epinephrine HCl, Epipodophylotoxin (VP-16-213), Epirubicin HCl, Epoetin Alfa, Epoprostenol Sodium, Eptifibatide, Ergonovine Maleate, Ergotamine Tartrate, Ertapenem, Erythromycin Gluceptate, Erythromycin Lactobionate, Esmolol HCl, Esomeprazole Sodium, Ethacrynate Sodium, Ethanolamine Oleate, Etidronate Disodium, Etomidate, Etoposide, Etoposide Phosphate, Famotidine, Fat Emulsion, Fenoldopam Mesylate, Fentanyl Citrate, Fentanyl Citrate And Droperidol, Filgrastim, FK 506, Floxacillin, Floxuridine, Fluconazole, Flucytosine, Fludarabine Phosphate, Flumazenil, Fluorouracil, Fluphenazine HCl, Folic Acid, Folic Acid, Sodium Salt, Fosaprepitant Dimeglumine, Foscarnet Sodium, Fosphenytoin Sodium, Freamine II, Freamine III, Furosemide, Galactose, Gallium Nitrate, Ganciclovir Sodium, Gatifloxacin, Gemcitabine HCl, Gentamicin Sulfate, Globulin, Immune (Human), Glycopyrrolate, Gold Sodium Thiomalate, Gold Sodium Thiosulfate, Granisetron HCl, Haloperidol Lactate, Heparin Sodium, Heroin HCl, Hetastarch, Hetastarch In Lactated Electrolyte Injection, Hyaluronidase, Hydralazine HCl, Hydrochloric Acid, Hydrocortisone Sodium Phosphate, Hydrocortisone Sodium Succinate, Hydromorphone HCl, Hydroxyzine HCl, Hyoscine Butylbromide, Hyperalimentation Solutions, Ibuprofen, Ibutilide Fumarate, Idarubicin HCl, Ifosfamide, Imipenem-Cilastatin Sodium, Immune Globulin Intravenous (Human), Inamrinone Lactate, Indigotindisulfonate Sodium, Indomethacin Sodium Trihydrate, Infliximab, Insulin Aspart, Insulin Lispro, Insulin, Regular, Interferon Alfa-2a, Interferon Alfa-2b, Interleukin-2, Recombinant, Intralipid, Iodipamide (Sodium And Meglumine), Iproplatin, Irinotecan HCl, Iron Dextran, Iron Sucrose, Isoproterenol HCl, Isosorbide Dinitrate, Itraconazole, Kanamycin Sulfate, Ketamine HCl, Ketoprofen, Ketorolac Tromethamine, Labetalol HCl, Lansoprazole, Leucovorin Calcium, Levallorphan Tartrate, Levetiracetam, Levobupivacaine, Levocarnitine, Levodopa, Levofloxacin, Levoleucovorin Calcium, Levorphanol Tartrate, Levothyroxine Sodium, Lidocaine HCl, Lincomycin HCl, Linezolid, Liposyn II, Lorazepam, Magnesium Sulfate, Mannitol Solution, Mechlorethamine HCl, Melphalan, Menadiol Sodium Diphosphate, Menadione Sodium Bisulfite, Menotropins, Meperidine HCl, Mercaptopurine Sodium, Meropenem, Mesna, Metaraminol Bitartrate, Methacholine Chloride, Methadone HCl, Methicillin Sodium, Methocarbamol, Methohexital Sodium, Methotrexate Sodium, Methotrimeprazine HCl, Methoxamine HCl, Methyldopate HCl, Methylergonovine Maleate, Methylprednisolone Sodium Succinate, Metoclopramide HCl, Metoprolol Tartrate, Metronidazole HCl, Mezlocillin Sodium, Micafungin Sodium, Miconazole, Midazolam HCl, Milrinone Lactate, Minocycline HCl, Mithramycin, Mitomycin, Mitoxantrone HCl, Mivacurium Chloride, Morphine HCl, Morphine Sulfate, Morphine Tartrate, Moxalactam Disodium, Moxifloxacin HCl, Multiple Vitamin Infusion, MVI-12, Mycophenolate Mofetil HCl, N Methylformamide, N, N-Dimethylacetamide, Nafcillin Sodium, Nalbuphine HCl, Naloxone HCl, Neostigmine Methylsulfate, Nesiritide, Netilmicin Sulfate, Nicardipine HCl, Nitrofurantoin Sodium, Nitroglycerin, Nitroprusside Sodium, Nizatidine, Norepinephrine Bitartrate, N-Phosphoacetyl-L-Aspartate (Pala), Octreotide Acetate, Ofatumumab, Ofloxacin, Omeprazole Sodium, Ondansetron HCl, Opium Alkaloids, Mixed, Orphenadrine Citrate, Oxacillin Sodium, Oxaliplatin, Oxycodone HCl, Oxymorphone HCl, Oxytocin, Paclitaxel, Palonosetron HCl, Pamidronate Disodium, Pancuronium Bromide, Panitumumab, Pantoprazole Sodium, Papaverine HCl, Paraldehyde, Parenteral Nutrition Admixtures, Pemetrexed, Penicillin G Potassium, Penicillin G Sodium, Pentamidine Isethionate, Pentazocine Lactate, Pentobarbital Sodium, Pentostatin, Perfluorochemical Emulsion, Peritoneal Dialysis Solutions, Perphenazine, Pertuzumab, Phenobarbital Sodium, Phentolamine Mesylate, Phenylephrine HCl, Phenytoin Sodium, Phosphonoformate, Phytonadione, Piperacillin And Tazobactam, Piperacillin Sodium, Plicamycin, Polymyxin B Sulfate, Potassium Acetate, Potassium Chloride, Potassium Phosphate, Pralidoxime Chloride, Prednisolone Sodium Phosphate, Procainamide HCl, Procaine HCl, Prochlorperazine Edisylate, Prochlorperazine Mesylate, Promazine HCl, Promethazine HCl, Propafenone HCl, Propofol, Propranolol HCl, Protamine Sulfate, Protein Hydrolysate, Pyridostigmine Bromide, Pyridoxine HCl, Quinidine Gluconate, Quinidine Sulfate, Quinupristin And Dalfopristin, Ranitidine HCl, Remifentanil HCl, Reserpine, Reteplase, Riboflavin, Rifampin, Ritodrine HCl, Rituximab, Rocuronium Bromide, Romidepsin, Ropivacaine HCl, Sargramostim, Scopolamine Hydrobromide, Secobarbital Sodium, Sildenafil Citrate, Sodium Acetate, Sodium Ascorbate, Sodium Bicarbonate, Sodium Chloride, Sodium Citrate, Sodium Glycolate, Sodium Iodide, Sodium Lactate, Sodium Phosphate, Sodium Thiosulfate, Somatropin, Sotalol HCl, Streptokinase, Streptomycin Sulfate, Streptozocin, Succinylcholine Chloride, Sufentanil Citrate, Sulfamethoxazole-Trimethoprim, Sulfisoxazole Diethanolamine, Sumatriptan Succinate, Suramin, Tacrolimus, Teicoplanin, Telavancin, Temsirolimus, Tenecteplase, Teniposide, Terbutaline Sulfate, Teriparatide Acetate, Tetracaine HCl, Tetracycline HCl, Theophylline, Premixed, Thiamine HCl, Thiethylperazine Maleate, Thiopental Sodium, Thioridazine HCl, Thiotepa, Thiothixene HCl, Ticarcillin Disodium, Ticarcillin Disodium-Clavulanate Potassium, Tigecycline, Tirofiban HCl, Tobramycin Sulfate, Tolazoline HCl, Topotecan HCl, Torsemide, Total Parenteral Nutrition Solutions, Trace Element Solution, Tramadol HCl, Tranexamic Acid, Trastuzumab, Travasol, Treprostinil Sodium, Trifluoperazine HCl, Triflupromazine HCl, Trimethobenzamide HCl, Trimetrexate Glucuronate, Tromethamine, Trophamine, Tryptophan, Tubocurarine Chloride, Urokinase, Valproate Sodium, Vancomycin HCl, Vasopressin, Vecuronium Bromide, Verapamil HCl, Vidarabine, Vinblastine Sulfate, Vincristine Sulfate, Vinorelbine Tartrate, Vitamin A, Vitamin B Complex, Vitamin B Complex With C, Vitamin E, Vitamin K, Voriconazole, Warfarin Sodium, Ziconotide, Zidovudine, and combination thereof.

It may be another aspect of the invention that a drug delivery device for the delivery of independently user selectable variable doses of the first medicament (1aa) and second medicament (11aa) may have the following key features. (i) In one of the embodiments individual variable dose setting mechanism may be provided for each of the first medicament (1aa) and second medicament (11aa) contained in cartridges of their respective chambers/medicament reservoirs; (ii) a single activation button operably connected to a single dispensing interface may be provided for the delivery of first medicament (1aa) and second medicament (11aa) from their respective medicament chambers/medicament reservoirs; (iii) the locking and unlocking mechanisms for the first medicament (1aa) and the second medicament (11aa) may be linked with their respective dose setters of the dose setting mechanisms for their functionality; (iv) there may be provided individual unlocking for each of the dose setters of the first medicament (1aa) and second medicament (11aa); (v) each of the dose setters of the first medicament (1aa) and second medicament (11aa) may be able to be operated only after the unlocking of their respective locking mechanism; (vi) after the completion of the delivery of the first medicament (1aa) and second medicament (11aa) of their set doses due to user action of single activation button, the respective dose setters may get automatically locked. The features (i) to (vi) of the drug delivery device of the invention further may render the delivery of medicament (1aa) and medicament (11aa) either alone or together depending on whether the selected doses are unequal or equal. The possible ways of delivery of medicament (1aa) and medicament (11aa) may be as follows; (a) In one of the embodiments variable drug delivery of medicament (1aa) and medicament (11aa) with equal set dose may be delivered; for example either 5, 10, 15 and 20 IU etc, equal doses of both the medicament (1aa) and medicament (11aa) may be delivered; (b) In another embodiment variable drug delivery of medicament (1aa) and medicament (11aa) with different doses may be delivered; for example each of the doses of medicament (1aa) and medicament (11aa) may be in combinations of 15 and 5 IU, 20 and 5 IU and the like; (c) In another embodiment variable drug delivery from medicament (1aa) may be delivered while medicament (11aa) may be locked; (d) In yet another embodiment variable drug delivery from medicament (11aa) may be delivered while medicament (1aa) may be locked.

It may be yet another aspect of an invention that an embodiment of the drug delivery device may be able to deliver three or more medicaments. The drug delivery device for delivery of three medicaments comprising independently user selectable variable doses of the first medicament (1aa), independently user selectable variable doses of the second medicament (11aa) and user selectable fixed doses of the third medicament (111aa) of the invention may have the following key features; (i) individual variable dose setting may be provided for each of the first medicament (1aa) and second medicament (11aa) contained in cartridges of their chambers/medicament reservoirs; a separate user selectable fixed dose setting may be provided for the third medicament (111aa) contained in the cartridge chamber/reservoir; (ii) a single activation button operably connected to a single dispensing interface may be provided for the delivery of first medicament (1aa), second medicament (11aa) and third medicament (111aa) from their respective medicament chambers/medicament reservoirs; (iii) the locking mechanisms and unlocking mechanisms for the first medicament (1aa), the second medicament (11aa) and third medicament (111aa) may be linked with their respective dose setters for their functionality; (iv) there may be provided individual unlocking for each of the dose setters of the first medicament (1aa), second medicament (11aa) and third medicament (111aa); (v) each of the dose setters of the first medicament (1aa), second medicament (11aa) and third medicament (111aa) may be operated only after the unlocking of their respective locking mechanisms; (vi) after the completion of the delivery of the first medicament (1aa), second medicament (11aa) and third medicament (111aa) of their set doses due to user action of single activation button, the respective dose setters may get automatically locked.

The features of (i) to (vi) of the drug delivery device of the invention to deliver three medicaments may render delivery of first medicament (1aa), second medicament (11aa) and third medicament (111aa) either alone or together depending on whether doses set equal or unequal. The possible ways of delivery of medicament (1aa), medicament (11aa) and medicament (111aa) may be as follows; (a) In one of the embodiments variable drug delivery of medicament (1aa) and medicament (11aa) with equal doses may be delivered by the activation of single activation button by the user while medicament (111aa) may be locked; (b) In another embodiment variable drug delivery of medicament (1aa) and medicament (11aa) with different doses may be delivered by the activation of single activation button by the user while medicament (111aa) may be locked; (c) In another embodiment variable drug delivery of medicament (1aa) may be delivered by the activation of single activation button by the user while medicament (11aa) and medicament (111aa) may be locked; (d) In another embodiment variable drug delivery of medicament (11aa) may be delivered by the activation of single activation button by the user while medicament (1aa) and medicament (111aa) may be locked; (e) In another embodiment variable drug delivery of medicament (1aa) and fixed dose drug delivery of medicament (111aa) may be delivered by the activation of single activation button by the user while medicament (11aa) may be locked; (f) In another embodiment variable drug delivery of medicament (11aa) and fixed dose drug delivery of medicament (111aa) may be delivered by the activation of single activation button by the user while medicament (1aa) may be locked; (g) In another embodiment fixed dose drug delivery of medicament (111aa) may be delivered by the activation of single activation button by the user while medicament (1aa) and medicament (11aa) may be locked; (h) In yet another embodiment variable drug delivery of medicament (1aa), medicament (11aa) and fixed dose of medicament (111aa) may be delivered by the activation of single activation button by the user.

In the embodiment of drug delivery device to deliver two independently user selectable medicaments within a single device through a single dispense interface, the device has a cylindrical housing comprising a user operable variable dose setter operably connected to a medicament reservoir comprising a cartridge containing the first medicament (1aa) containing one or more doses; Similarly the device has a separate cylindrical housing comprising a user operable variable dose setter operably connected to a separate medicament reservoir comprising a separate cartridge containing the second medicament (11aa) containing one or more doses. Each one of the medicament reservoirs of the first medicament (1aa) and second medicament (11aa) of drug delivery device may comprise a separate dose setting mechanism comprising a cylindrical dose setter provided towards the proximal end of a cylindrical dose drum. The dose drums of the first medicament (1aa) and second medicament (11aa) may have inward helical grooves provided on their external circumferential surface running from a proximal portion to distal portion of the dose drum. The dose drums further may have longitudinal groves provided on their proximal portion. The longitudinal grooves of the first medicament (1aa) and second medicament (11aa) dose drums may extend from the initial position of the helical grooves in the proximal portion and may terminate before the immediate distal inward helical grooves (FIG. 1; 3b, 33b). The longitudinal grooves initial position and helical grooves start point on the proximal portion of the dose drums may be one and the same. During dose selection the dose drums may rotate in the clockwise direction when the inward helical grooves may be provided whereas the dose drums may rotate in the opposite direction i.e. anti clockwise direction when the outward helical grooves may be provided.

The drug delivery device for delivery of two medicaments further may comprise a first medicament (1aa) dose delivery mechanism enclosed in a cylindrical housing, a user operable variable dose locking mechanism mounted on a cylindrical housing and operably connected to the dose setter of the dose setting mechanism; and a second medicament (11aa) dose delivery mechanism enclosed in another cylindrical housing, a separate user operable variable dose locking mechanism mounted on the separate cylindrical housing and operably connected to the second dose setter of the dose setting mechanism.

Each one of drug delivery device user operable variable dose locking mechanisms of the first medicament (1aa) and second medicament (11aa) contained in the cartridges of the medicament reservoirs of the drug delivery device may comprise the components a knob, a bracket and a spring. The user operable variable dose locking mechanism may is capable of locking and unlocking the dose setting mechanism which in turn make active the dose delivery mechanism. The knob may assume different positions during the locking and unlocking of the dose setting mechanism. The function of the spring may be to achieve the automatic locking of dose setter after the delivery of the set dose and the counter level of the dose drum may reach zero position. The spring may assume compressed position during unlocking and would be in a relaxed position during locked condition. The function of the knob may be to unlock the locking mechanism. The bracket may be for supporting the knob and the spring. The brackets of the locking mechanisms of first medicament (1aa) and second medicament (11aa) may be mounted on the outer surfaces of their respective housings firmly towards their proximal portion. The brackets may be held firmly on the outer surfaces of the housings by welding/integral moulding/snap fitting. The brackets may be of any shape such as rectangular, square, trapezoidal, oval etc. In the embodiment of the invention as shown in FIG. 1 to FIG. 16 the brackets may be of rectangular shape. The brackets may be bound by bracket longitudinal surfaces and bracket transverse surfaces which may be parallel to one another forming a rectangular shape within which the knobs and springs may be located.

The knobs may be bounded by knobs upper surface at the top, knobs lower surface at the bottom, knobs vertical surface at its side towards their distal end and knobs protrusion projecting downwardly from somewhere in the middle portion of the knob lower surface. The knobs may be arrested within the bracket. The knobs may be located towards the distal end of the bracket. The intention may that the knobs should not come off during their usage. The knobs may be the key components which establish contact with the dose drums of the dose setting mechanisms of the drug delivery device by mating of the knobs protrusions with the longitudinal grooves or inward helical grooves during the locking or unlocking of the user operable variable dose locking mechanisms.

The dose setters of the first medicament (1aa) and second medicament (11aa) may be locked when the knobs protrusions of the knobs align with the dose drum longitudinal grooves of the dose drums. In the lock condition the knobs vertical surfaces bias the bracket distal transverse surfaces. The dose setters may be unlocked when the knob protrusions of the knobs align with the dose drum helical grooves of the dose drums on sliding the knobs in the proximal direction.

The cartridge containing the first medicament (1aa) of the medicament reservoir and the cartridge containing the second medicament (11aa) of the separate medical reservoir may be operatively connected to common needle hub comprising a single needle. The selected doses of the first medicament (1aa) and second medicament (11aa) may be delivered through a common needle hub through a single needle on activation of single activation button through a single dispensing interface.

In the embodiment of the drug delivery device for delivery of two medicaments the dose setter of the first medicament (1aa) dose setting mechanism and the dose setter of the second medicament (11aa) dose setting mechanism may be operatively connected to the single activation button and the single dispensing interface which may facilitate the delivery of the first medicament (1aa) and the second medicament (11aa) simultaneously when equal doses may be selected. When there may be unequal selection of doses of the first medicament (1aa) and the second medicament (11aa), the higher dose medicament may be delivered initially until its remaining dosage matches the other medicament selected dosage, and simultaneous delivery of both the medicaments takes place till the completion of the doses (FIG. 3 and FIG. 4). For example if the dosage of first medicament (1aa) selected may be say 40 International units of insulin and the second medicament (11aa) selected may be say 20 international units of insulin analogue, the drug delivery device of the invention may deliver 20 international units of insulin alone first followed by 20 international units insulin and insulin analogue together simultaneously on activation of single activation button through a single dispensing interface.

User operable dose locking mechanism may be either user operable variable dose locking mechanism or user operable fixed dose locking mechanism. The user operable dose locking mechanism may be capable of locking and unlocking the dose setting mechanism and dose delivery mechanism.

Terminologies used in the present invention may be as follows. "User operable variable dose locking mechanism" as used in the drug delivery device of the invention may refer to the locking mechanism used for delivery of medicaments (1aa, 11aa) whose doses the user can vary as per the requirement contained in cartridges (1a, 11a) which may be contained in the medicament reservoirs (1, 11). The user may be able to set independently the variable doses by operating the dose setters as per the requirement after unlocking their respective locking mechanisms.

"User operable fixed dose locking mechanism" as used in the drug delivery device of the invention may refer to the locking mechanism used for delivery of fixed doses of medicament (111aa) contained in the cartridge (111a) which may further be contained in the medicament reservoir (111). The user may be able to set only the fixed dose by operating the dose setter after unlocking the locking mechanism.

The components employed and the way of functioning of both "User operable variable dose locking mechanism" and "User operable fixed dose locking mechanism" may be one and the same with regard to locking and unlocking.

Proximal portion or proximal end of a component or sub component or the drug delivery device may refer to dose setting portion or the dose setting end of the drug delivery device.

Distal portion or distal end of a component or sub component or the drug delivery device may refer to the delivery portion or delivery end of the drug delivery device.

An activation mechanism may be a single activation button.

Medicament as used in this invention may refer to one or more than one therapeutically active pharmaceutical ingredient or a combination thereof. For example each one of the first medicament (1aa), second medicament (11aa) and third medicament (111aa) may comprise either one therapeutically active pharmaceutical ingredient or more than one therapeutically active pharmaceutical ingredient.

Described below are the embodiments of the present invention. The various embodiments may only serve to illustrate the present invention. It should however be understood that they do not in any way restrict the scope of the invention. It may however be possible for a person skilled in the art to make obvious modifications to various components of drug delivery device, for example, changes to cartridge holder or to dose drum, housing etc. to arrive at a similarly functional design and the instant invention may be deemed to encompass all such modifications.

The embodiments of the drug delivery device which comprises (i) two user operable variable dose locking mechanisms and (ii) two user operable variable dose locking mechanisms and a user operable fixed dose locking mechanism of the invention are described in detail with references to the drawing. The invention described in detail with reference to FIG. 1 to FIG. 19 wherein the variable doses of the first medicament (1aa), second medicament (11aa) and the fixed dose of third medicament (111aa) may be one the embodiments to better illustrate the invention. However it could be possible in an another embodiment of the drug delivery device the user operable variable dose locking mechanism may be for one of the medicaments and user operable fixed dose locking mechanisms may be for two of the medicaments. There may be yet another embodiment of the drug delivery device wherein all the three medicaments may have either user operable variable dose locking mechanisms or user operable fixed dose locking mechanisms. The invention may be deemed to encompass all such modifications.

BRIEF DESCRIPTION OF THE DRAWING

The above mentioned and other advantages and objects of the invention, and the manner of attaining them, will become more apparent, and the invention will be better understood by reference to the following description of the embodiments of the invention taking in conjunction with the accompanying figures, wherein.

Figure 1:
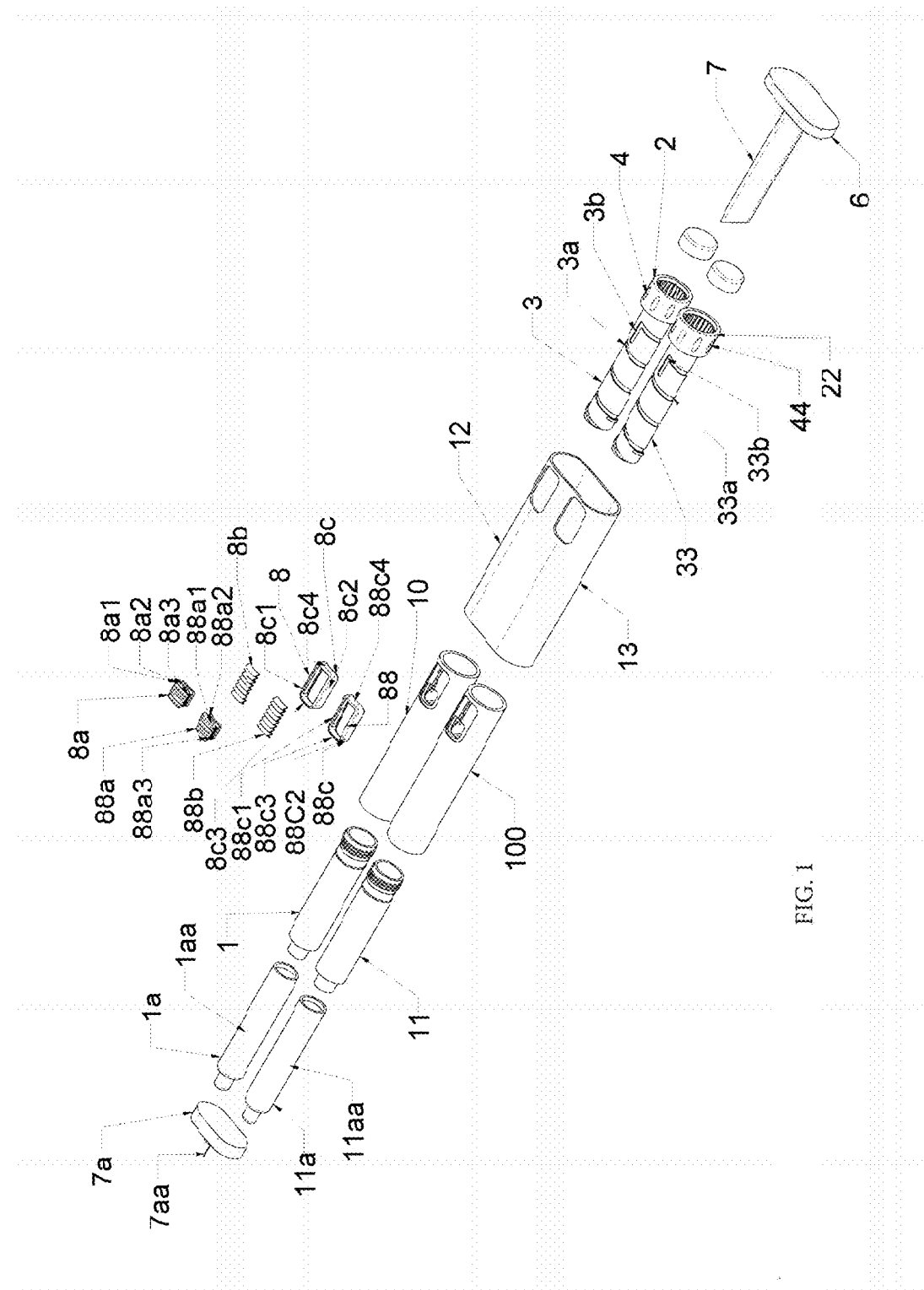
FIG. 1—Exploded perspective view of locking mechanism components linked with variable dose setters on medicament reservoir (1) and medicament reservoir (11) in a drug delivery device of FIG. 13 for delivery of medicament (1aa) and medicament (11aa) by a single activation through a single interface.
Figure 2:
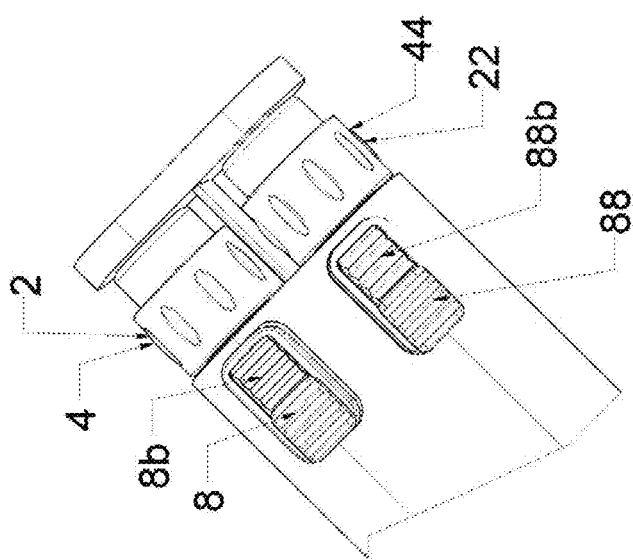
FIG. 2—Perspective view of locking mechanism linked with variable dose setters in lock condition with zero doses set shown on the medicament reservoir (1) and medicament reservoir (11) in a drug delivery device of FIG. 13 for delivery of medicament (1aa) and medicament (11aa) by a single activation through a single interface.
Figure 3:
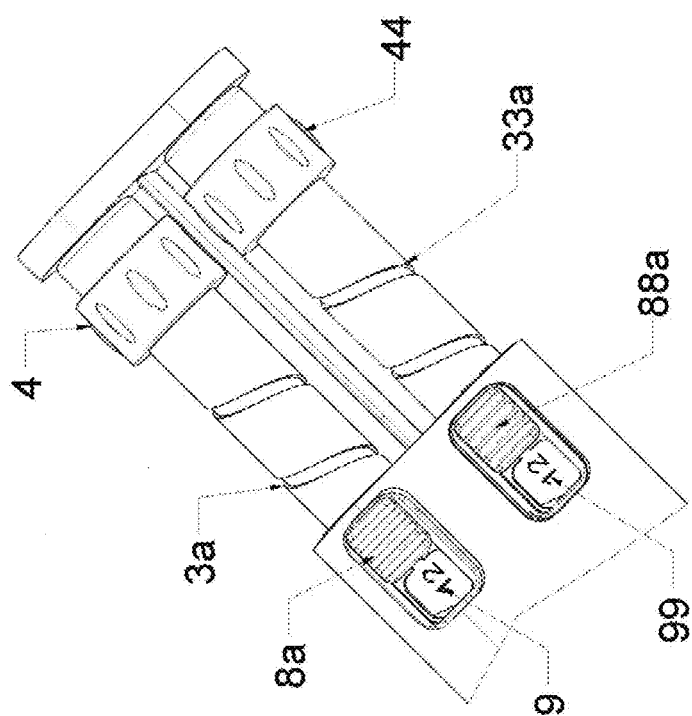
FIG. 3—Perspective view of locking mechanism linked with variable dose setters in unlock condition with equal variable doses set shown on medicament reservoir (1) and medicament reservoir (11) in a drug delivery device of FIG. 13 for delivery of medicament (1aa) and medicament (11aa) by a single activation through a single interface.

Although the figures represent embodiments of the present invention, the figures are not necessarily to scale, and certain features may be exaggerated or omitted in some of the figures in order to better illustrate and explain the present invention.

DETAILED DESCRIPTION OF THE INVENTION

The detailed description of a drug delivery device (12) of the invention for delivery of two medicaments, medicament (1aa), medicament (11aa) comprising user operable variable dose locking mechanism (8) and user operable variable dose locking mechanism (88) may be described as follows referring to FIG. 1 to FIG. 17. The drug delivery device (12) of the invention for delivery of two independently user selectable multiple doses of medicament (1aa) and medicament (11aa), may be contained in cartridge (1a) and cartridge (11a), of the medicament reservoir (1) and medicament reservoir (11); a user operable variable dose locking mechanism (8) associated with medicament (1aa) and a user operable variable dose locking mechanism (88) associated with medicament (11aa) may be mounted on the housing (10) and housing (100) within a single device operatively connected to a single dispense interface (7); the device comprises a dose setter (4), a dose drum (3) of the dose setting mechanism (2) contained within the housing (10); a dose setter (44), a dose drum (33) of the dose setting mechanism (22) contained within the housing (100); the device further comprises a dose delivery mechanism (5) operably connected to the dose setting mechanism (2) and a dose delivery mechanism (55) operably connected to the dose setting mechanism (22); wherein the user operable variable dose locking mechanism (8) mounted on the housing (10) may be operably connected to the dose setter (4) and the user operable variable dose locking mechanism (88) mounted on the housing (100) may be operably connected to the dose setter (44) which allow the selection of the appropriate doses of medicament (1aa) on unlocking the user operable variable dose locking mechanism (8) and selection of the appropriate doses of medicament (11aa) on unlocking the user operable variable dose locking mechanism (88); activation of single activation button (6) may dispense the selected doses of medicament (1aa) and medicament (11aa) and on completion of dispensation of doses user operable variable dose locking mechanism (8) and user operable variable dose locking mechanism (88) automatically get locked. The medicament (1aa) and medicament (11aa) may be delivered through a needle (7aa) attached to a common needle hub (7a). The needle hub (7a) may operably be connected to the medicament reservoir (1) and medicament reservoir (11).

Figure 9:
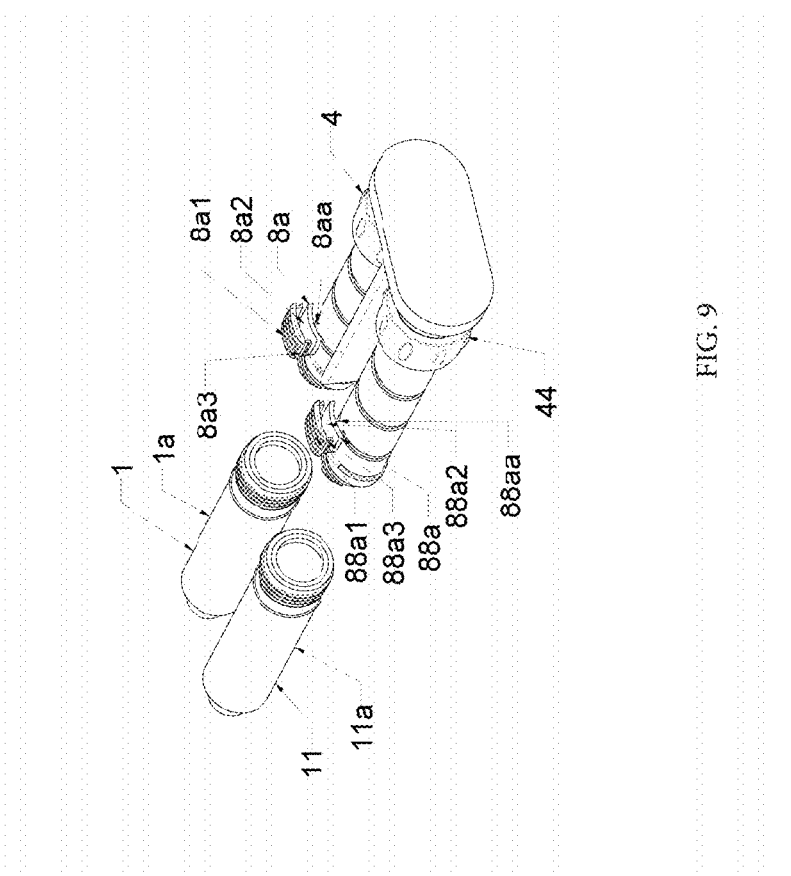
FIG. 9—Exploded view of sliding knob of locking mechanism linked with variable dose setters in the unlock condition with equal doses set shown on medicament reservoir (1) and medicament reservoir (11) in a drug delivery device of FIG. 13 for delivery of medicament (1aa) and medicament (11aa) by a single activation through a single interface.
Figure 12:
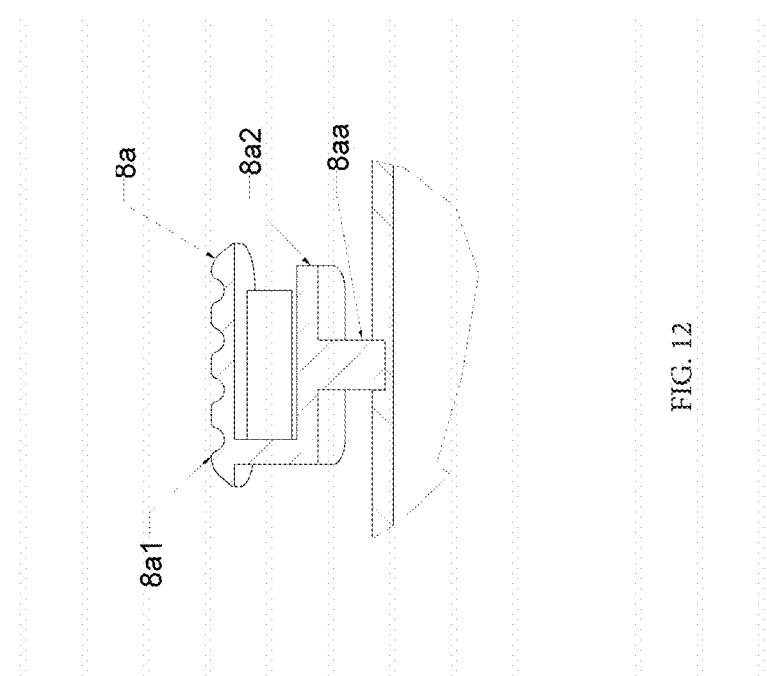
FIG. 12 Shows an enlarged view of details at "E" of FIG. 11.
Figure 13:
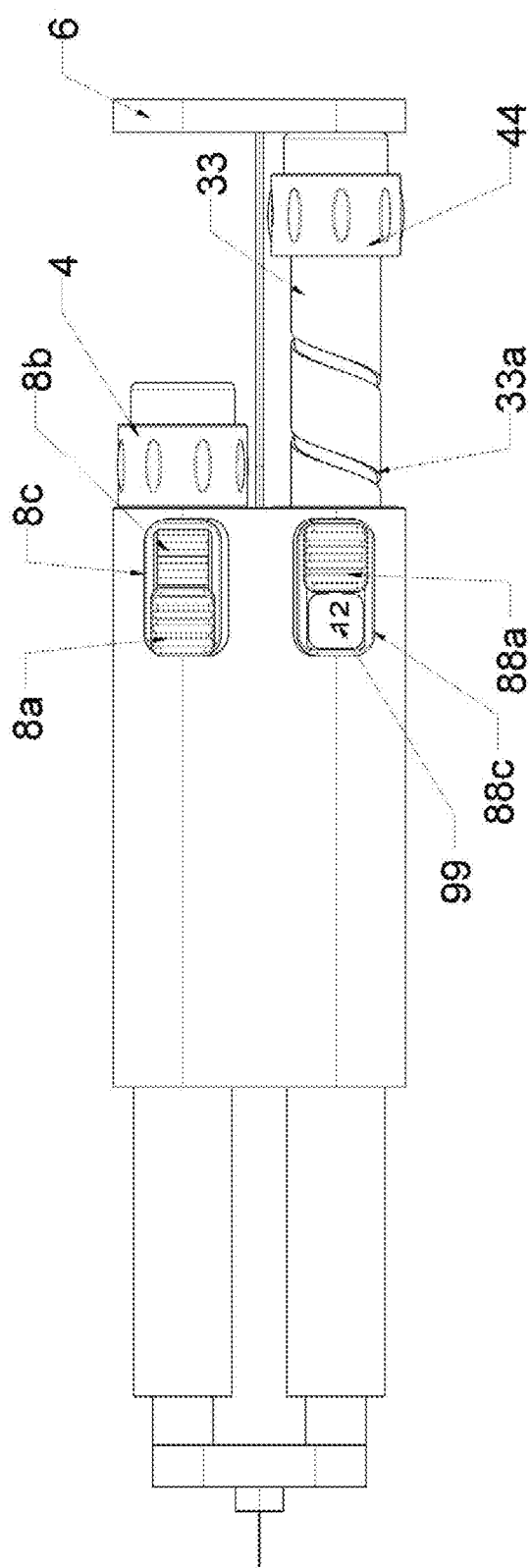
FIG. 13—Shows locking mechanisms linked with a variable dose setter in a lock condition with no dose set on the medicament reservoir (1) and variable dose setter in unlock condition with a variable dose set on the medicament reservoir (11) in a drug delivery device for delivery of medicament by a single activation through a single interface.
Figure 14:
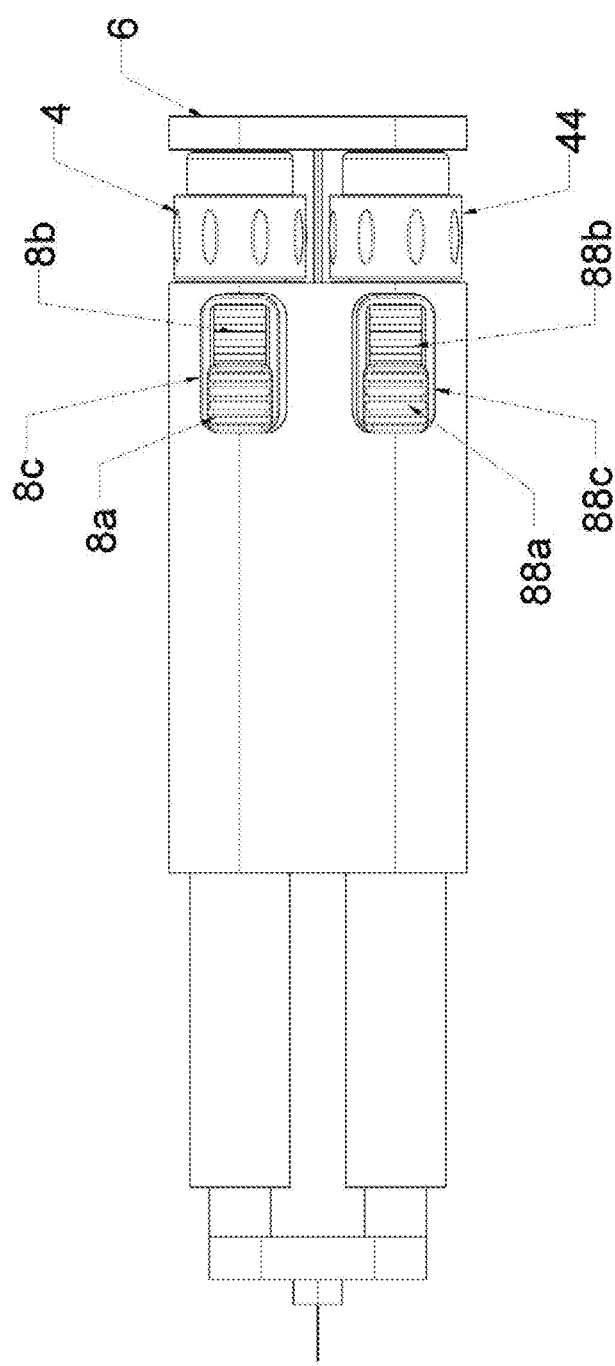
FIG. 14—Shows locking mechanisms linked with variable dose setters in lock conditions with no doses set on medicament reservoir (1) and medicament reservoir (11) in a drug delivery device for delivery of medicament by a single activation through a single interface.
Figure 15:
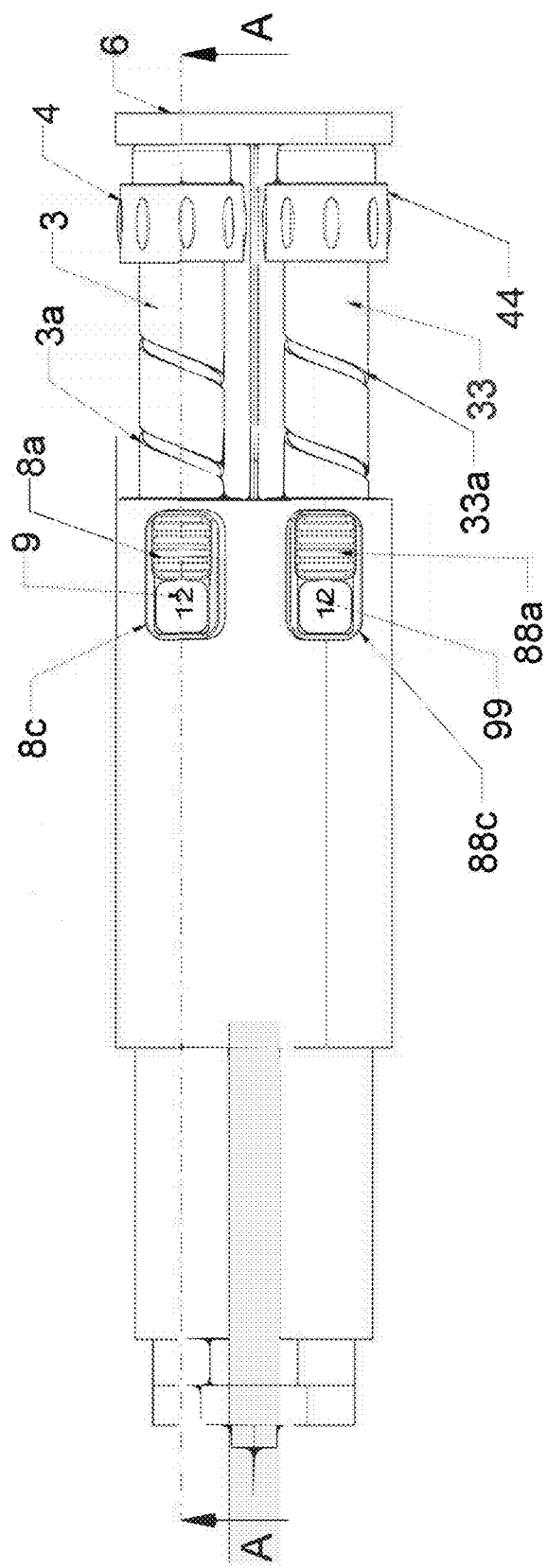
FIG. 15—Shows locking mechanisms linked with variable dose setters in unlock conditions with equal variable doses set on medicament reservoir (1) and medicament reservoir (11) in a drug delivery device for delivery of medicament by a single activation through a single interface.

Referring to FIG. 1, FIG. 9 and FIG. 13 the user operable variable dose locking mechanism (8) of the first medicament (1aa) contained in the cartridge (1a) of the medicament reservoir (1) of the drug delivery device (12) may comprise a knob (8a), a spring (8b) and a bracket (8c). The bracket (8c) of the locking mechanism (8) of the first medicament (1aa) contained in the cartridge (1a) of the medicament reservoir (1) may be mounted on the outer surface of the housing (10) firmly towards its proximal portion. The bracket (8c) may be held firmly on the outer surface of the housing (10) by welding/integral moulding/snap fitting. The bracket (8c) may be of any shape such as rectangular, square, trapezoidal, oval etc. In the embodiment of the invention as shown in FIG. 1 to FIG. 16 the brackets may be of rectangular shape. The bracket (8c) may be bound by bracket longitudinal surfaces (8c1, 8c2) and bracket transverse (8c3, 8c4) surfaces which may be parallel to one another forming a rectangular shape within which the knob (8a) and spring (8b) may be located. The spring (8b) may be of rectangular shape. Helical shaped spring (not shown in figure) may also be used. The function of the spring (8b) may be to achieve the automatic locking of dose setter (4) after the delivery of the set dose and the counter level of the dose drum (3) may reach zero position. The material property of the spring (8b) may be such that it may withstand repeated compression and relaxation during the use of the device. The proximal portion of the relaxed spring (8b) may be colored red. The knob upper surface (8a1) may be colored green. The distal portion of the spring (8b) may be held in place between the knob upper surface (8a1) and knob lower surface (8a2) and proximal portion of the spring (8b) may be held by bias with the proximal portion of the bracket transverse surface (8c4).

The knob (8a) may be bounded by knob upper surface (8a1) at the top, knob lower surface (8a2) at the bottom, knob vertical surface (8a3) at its side towards its distal end; a knob protrusion (8aa) may project downwardly closer to the middle portion of the knob lower surface (8a2). The knob (8a) may be arrested within the bracket (8c). The knob (8a) may be located towards the distal end of the bracket (8c) as shown in FIG. 2, FIG. 5 to FIG. 8, FIG. 13 and FIG. 14. The intention of placement of the knob (8a) within the bracket (8c) may be that the knob (8a) should not come off during its usage. The knob (8a) may be the key component which establish contact with the dose drum (3) of the dose setting mechanism (2) of the drug delivery device (12) by mating of the knob protrusion (8aa) with the longitudinal groove (3b) or inward helical groove (3a) of the dose drum (3) during the locking or unlocking of the user operable variable dose locking mechanism (8).

Referring to FIG. 1, FIG. 2, FIG. 5 to FIG. 8, FIG. 13 and FIG. 14, the user operable variable dose locking mechanism (8) of the drug delivery device (12) with the first medicament (1aa) inside the cartridge (1a) in its start position would be in the locked condition. In the lock condition the knob vertical surface (8a3) may bias the proximal end of the distal bracket transverse surface (8c3) by the distal end relaxation force of the spring (8b); further proximal end of the relaxed spring (8b) may mate with distal end of proximal bracket transverse surface (8c4); knob (8a) may be held in place due to this mating of the knob vertical surface (8a3) with distal bracket transverse surface (8c3) by the distal end relaxation force of the spring (8b) and the mating of proximal end of the relaxed spring (8b) with the distal end of proximal bracket transverse surface (8c4). And when this happens the knob protrusion (8aa), so located on the knob lower surface (8a2), may align with the proximal portion of the longitudinal groove (3b) of the dose drum (3).

Figure 4:
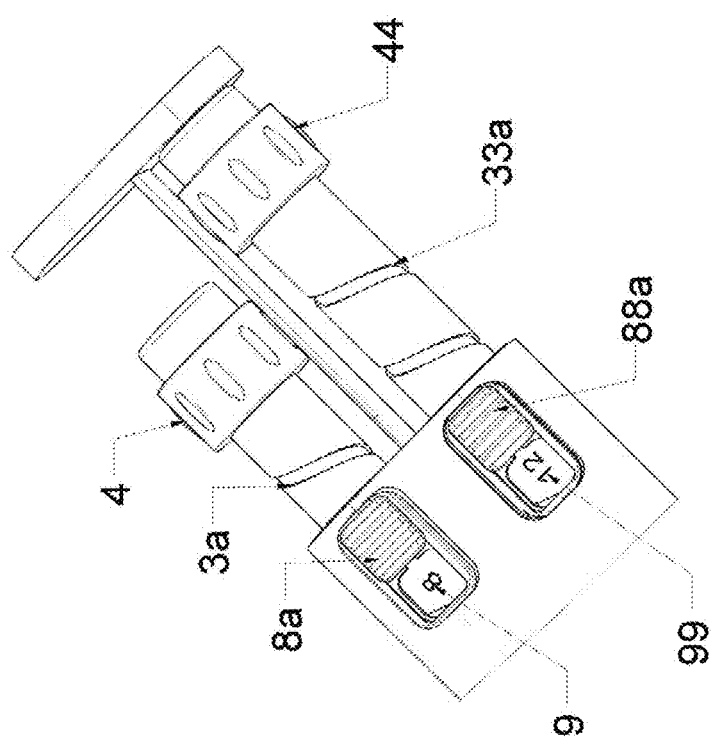
FIG. 4—Perspective view of locking mechanism linked with variable dose setters in unlock condition with unequal variable doses set shown on medicament reservoir (1) and medicament reservoir (11) in a drug delivery device of FIG. 13 for delivery of medicament (1aa) and medicament (11aa) by a single activation through a single interface.
Figure 5:
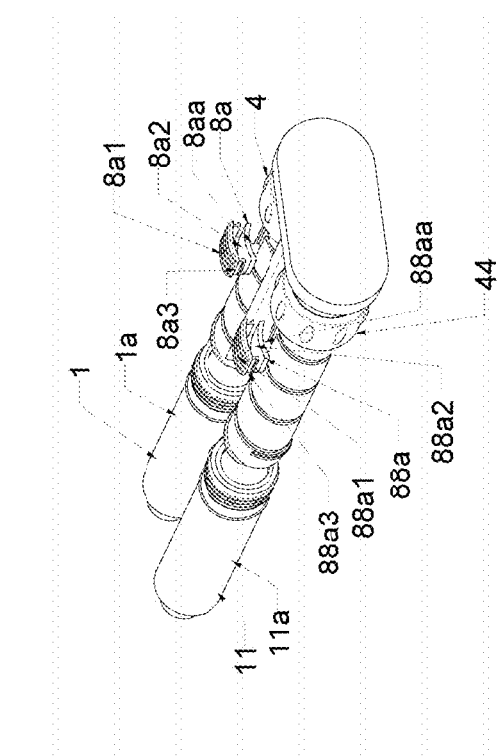
FIG. 5—Exploded view of a sliding knob of locking mechanism linked with variable dose setters in the lock condition ready for dose set operation shown on medicament reservoir (1) and medicament reservoir (11) in a drug delivery device of FIG. 13 for delivery of medicament (1aa) and medicament (11aa) by a single activation through a single interface.
Figure 6:
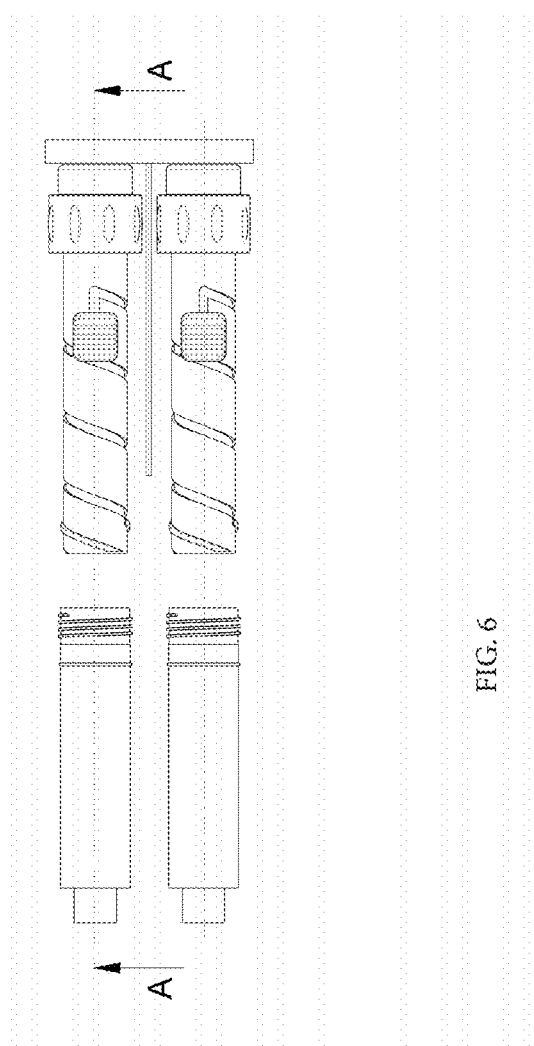
FIG. 6—Shows a perspective view of locking mechanism linked with variable dose setters in lock condition with no doses set on medicament reservoir (1) and medicament reservoir (11) in a drug delivery device of FIG. 13 for delivery of medicament (1aa) and medicament (11aa) by a single activation through a single interface.
Figure 7:
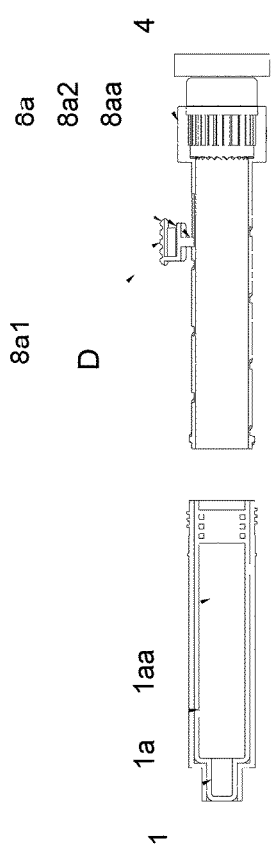
FIG. 7 Shows a sectional view along A-A of FIG. 6 on medicament reservoir (1) showing a sliding knob of locking mechanism linked with variable dose setter on medicament reservoir (1) in the lock condition ready for dose set operation to be commenced; the sectional view shows the details of mating of attachment knob (8a) with the dose drum longitudinal groove of the dose drum.
Figure 8:
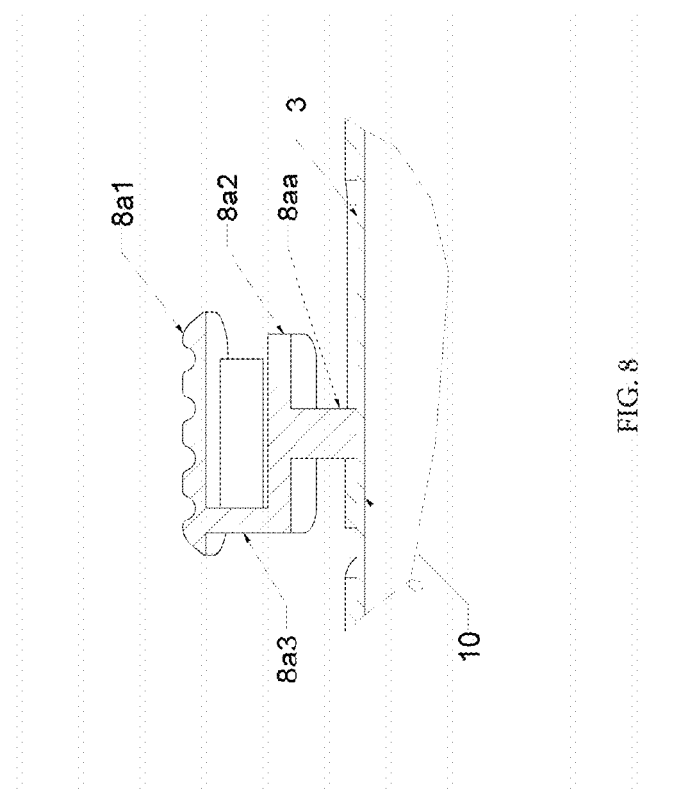
FIG. 8 shows an enlarged view of details at "D" of FIG. 7.
Figure 10:
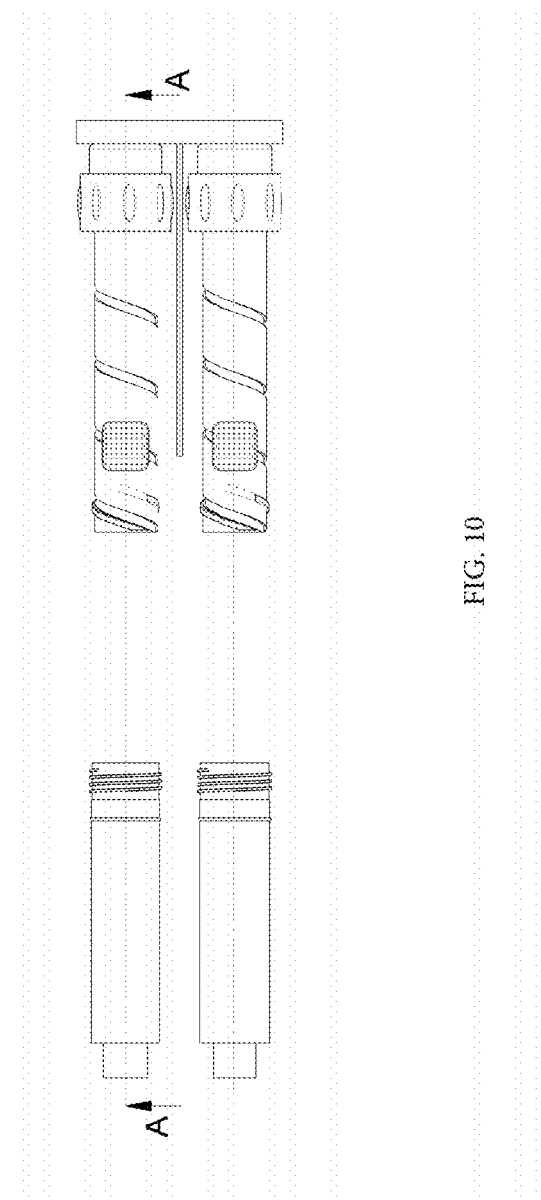
FIG. 10 Top view of FIG. 9 with variable dose setters in the unlock condition with equal doses set.
Figure 11:
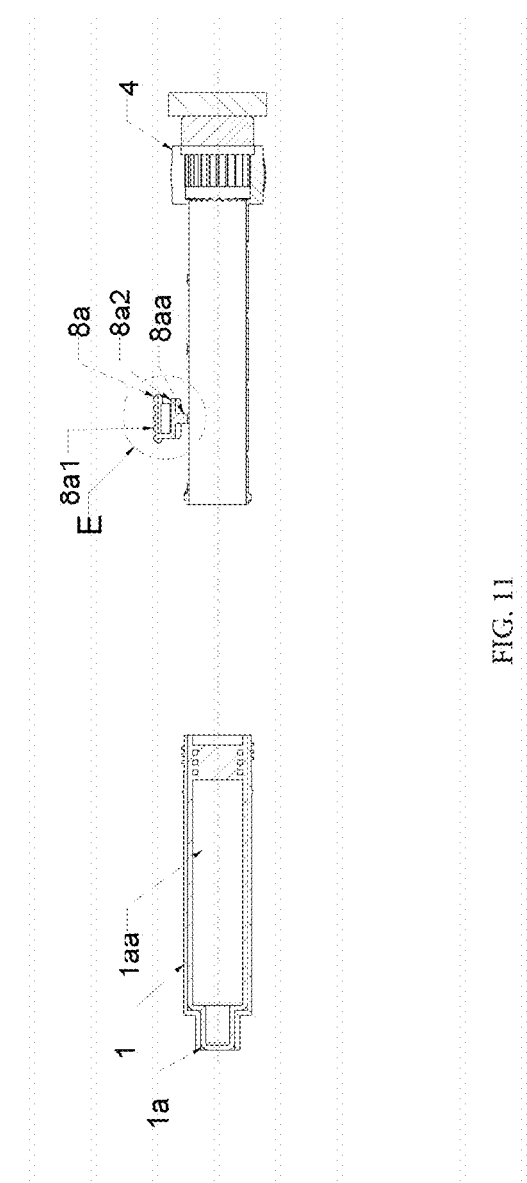
FIG. 11 Shows a sectional view along A-A of FIG. 10 on medicament reservoir (1) showing a sliding knob of locking mechanism linked with variable dose setter on medicament reservoir (1) in the unlock condition with variable dose set; the sectional view shows the details of mating of attachment knob (8a) with the dose drum helical groove of the dose drum.
Figure 16:
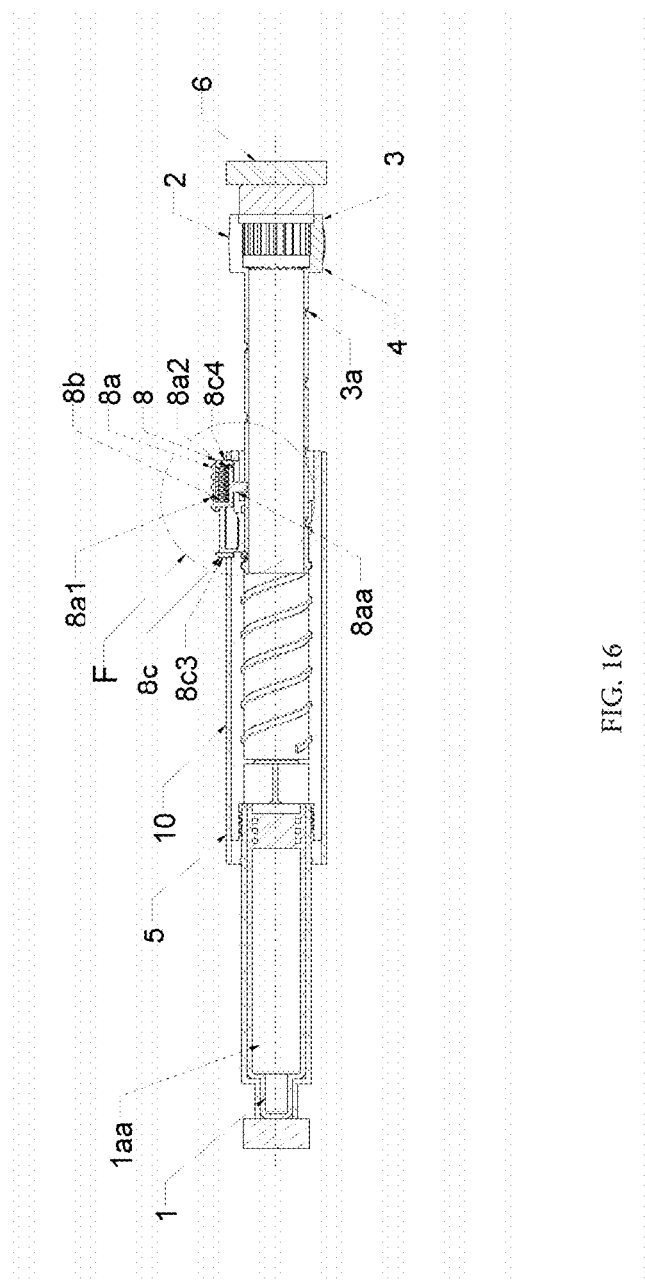
FIG. 16—Shows sectional view along A-A of FIG. 15 showing sliding knob of variable dose setter in unlock conditions with equal variable doses set on medicament reservoir (1) and medicament reservoir (11) in a drug delivery device by a single activation through a single interface.
Figure 17:
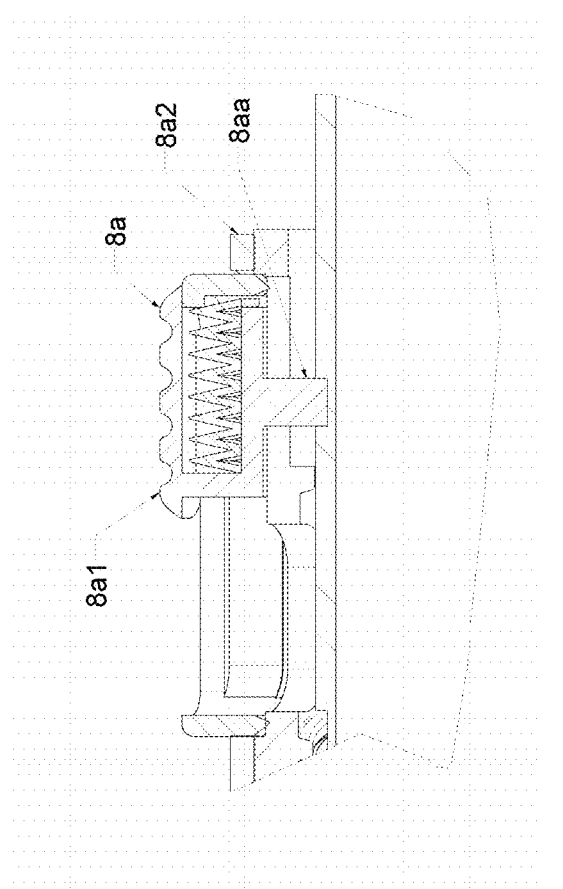
FIG. 17—Details at "F" of FIG. 16

Unlocking the user operable variable dose locking mechanism (8) may be described by referring to FIG. 1, FIG. 3, FIG. 4, FIG. 9, FIG. 10, FIG. 11, FIG. 12, FIG. 15, FIG. 16 and FIG. 17. Suppose a selected dose of the first medicament (1aa) may have to be administered, then the user operable variable dose locking mechanism (8) of the drug delivery device (12) would have to be unlocked to set the desired dose. To set a dose, the knob (8a) of the locking mechanism (8) may to have to be slided or pushed towards the proximal portion of the drug delivery device (12). By doing so, the knob protrusion (8aa) of the knob (8a) may travel along longitudinal groove (3b) of the dose drum (3) in the proximal direction from its initial locked position. This movement may push the knob (8a) towards the proximal portion compressing the flexible spring (8b). This may align the knob protrusion (8aa) with the initial position of the helical groove (3a) of the dose drum (3) as shown in FIG. 1. The proximal end of the longitudinal groove (3b) and the initial position in proximal portion of the helical groove (3a) may be one and the same. The knob protrusion (8aa) may take the immediate next position of the helical groove (3a) at the junction of the longitudinal groove (3b) and the proximal portion helical groove (3a) to support the compression force of the spring (8b). Further in the unlock condition the knob (8a) may be held in place in the bracket (8c) by the mating of the proximal portion or proximal end of the knob vertical surface (8a3) with the distal end of the spring (8b) in a compressed condition and the mating of the proximal end of the spring (8b) with the distal portion of the proximal bracket transverse surface (8c4). In the embodiment shown in FIG. 3 the desired dose of the medicament (1aa) may be set at 12 IU or at 8 IU as shown in FIG. 4 which may correspond to either the case of equal doses of medicine (1aa) and medicine (11aa) or the case of unequal doses of medicine (1aa) and medicine (11aa). Referring to FIG. 9, FIG. 10 it may be seen the knob protrusion (8aa) of the locking mechanism (8) and knob protrusion (88aa) of the locking mechanism (88) may have travelled the path of the helical groove (3a) and helical groove (33a) corresponding to the set dosage of the medicine (1aa) and medicament (11aa). During this dosage setting the spring (8b) of the locking mechanism (8) and spring (88) of the locking mechanism (88) (not shown in figure) would be in the compressed state as shown in FIG. 16 and FIG. 17 for medicament (1aa) and medicament (11aa). FIG. 11 and FIG. 12 show the position of the protrusion (8aa) in cross sectional view of FIG. 10.

Referring to FIG. 1, FIG. 9 and FIG. 13 the user operable variable dose locking mechanism (88) of the second medicament (11aa) contained in the cartridge (11a) of the medicament reservoir (11) of the drug delivery device (12) may comprise a knob (88a), a spring (88b) and a bracket (88c). The bracket (88c) of the locking mechanism (88) of the second medicament (11aa) contained in the cartridge (11a) of the medicament reservoir (11) may be mounted on the outer surface of the housing (100) firmly towards its proximal portion. The bracket (88c) may be held firmly on the outer surface of the housing (100) by welding/integral moulding/snap fitting. The bracket (88c) may be of any shape such as rectangular, square, trapezoidal, oval etc. In the embodiment of the invention as shown in FIG. 1 to FIG. 16 the brackets (8c, 88c) may be of rectangular shape. The bracket (88c) may be bound by bracket longitudinal surfaces (88c1, 88c2) and bracket transverse (88c3, 88c4) surfaces which may be parallel to one another forming a rectangular shape within which the knob (88a) and spring (88b) may be located. The spring (88b) may be of rectangular shape. Helical shaped spring (not shown in figure) may also be used. The function of the spring (88b) may be to achieve the automatic locking of dose setter (44) after the delivery of the set dose and the counter level of the dose drum (33) may reach zero position. The material property of the spring (88b) may be such that it may withstand repeated compression and relaxation during the use of the device (12). The proximal portion of the relaxed spring (88b) may be colored red. The knob upper surface (88a1) may be colored green. The distal portion of the spring (88b) may be held in place between the knob upper surface (88a1) and knob lower surface (88a2) and the proximal portion of the spring (88b) may be held by bias with proximal portion of the bracket transverse surface (88c4).

The knob (88a) may be bounded by knob upper surface (88a1) at the top, knob lower surface (88a2) at the bottom, knob vertical surface (88a3) at its side towards its distal end; a knob protrusion (88aa) may project downwardly closer to the middle portion of the knob lower surface (88a2). The knob (88a) may be arrested within the bracket (88c). The knob (88a) may be located towards the distal portion of the bracket (88c) as shown in FIG. 2, FIG. 5 to FIG. 6 and FIG. 14. The intention of placement of the knob (88a) within the bracket (88c) may be that the knob (88a) should not come off during its usage. The knob (88a) may be the key component which establish contact with the dose drum (33) of the dose setting mechanism (22) of the drug delivery device (12) by mating of the knob protrusion (88aa) with the longitudinal groove (33b) or inward helical groove (33a) of the dose drum (33) during the locking or unlocking of the user operable variable dose locking mechanism (88).

Referring to FIG. 2, FIG. 5, FIG. 6 and FIG. 14, the user operable variable dose locking mechanism (88) of the drug delivery device (12) with the second medicament (11aa) inside the cartridge (11a) in its start position would be in the locked condition. In the lock condition the knob vertical surface (88a3) may bias the proximal end of the distal bracket transverse surface (88c3) by the distal end relaxation force of the spring (88b); further proximal end of the relaxed spring (88b) may mate with distal end of proximal bracket transverse surface (88c4); knob (88a) may be held in place due to this mating of the knob vertical surface (88a3) with distal bracket transverse surface (88c3) by the distal end relaxation force of the spring (88b) and the mating of proximal end of the relaxed spring (88b) with the distal end of proximal bracket transverse surface (88c4). And when this happens the knob protrusion (88aa), so located on the knob lower surface (88a2), may align with the proximal portion of the longitudinal groove (33b) of the dose drum (33).

Unlocking of the user operable variable dose locking mechanism (88) may be described by referring to FIG. 1, FIG. 3, FIG. 4, FIG. 9, FIG. 10, FIG. 13 and FIG. 15. Suppose a selected dose of the second medicament (11aa) may have to be administered, then the user operable variable dose locking mechanism (88) of the drug delivery device (12) would have to be unlocked to set the desired dose. To set a dose, the knob (88a) of the locking mechanism (88) may to have to be slided or pushed towards the proximal portion of the drug delivery device (12). By doing so, the knob protrusion (88aa) of the knob (88a) may travel along longitudinal groove (33b) of the dose drum (33) in the proximal direction from its initial locked position. This movement may push the knob (88a) towards the proximal portion compressing the flexible spring (88b). This may align the knob protrusion (88aa) with the initial position of the helical groove (33a) of the dose drum (33) as shown in FIG. 1. The proximal end of the longitudinal groove (33b) and the initial position in proximal portion of the helical groove (33a) may be one and the same. The knob protrusion (88aa) may take the immediate next position of the helical groove (33a) at the junction of the longitudinal groove (33b) and the proximal portion helical groove (33a) to support the compression force of the spring (88b). Further in the unlock condition the knob (88a) may be held in place in the bracket (88c) by the mating of the proximal portion or the proximal end of the knob vertical surface (88a3) with the distal end of the spring (88b) in a compressed condition and the mating of the proximal end of the spring (88b) with the distal portion of the proximal bracket transverse surface (88c4). In the embodiment shown in FIG. 3 the desired dose of the medicament (11aa) may be set at 12 IU which may correspond to either the case of equal doses off first medicine (1aa) and second medicine (11aa) or the case of unequal doses of first medicine (1aa) and second medicine (11aa). Referring to FIG. 9, FIG. 10, FIG. 13 and FIG. 15 it may be seen the knob protrusion (88aa) of the locking mechanism (88) may have travelled the path of the helical groove (33a) corresponding the set dosage of the second medicine (11aa). During this dosage setting the spring (88b) of the locking mechanism (88) would be in the compressed state.

The administration/delivery of either the equal set doses of the first medicament (1aa) and second medicament (11aa) as shown in FIG. 3, FIG. 9, FIG. 10 and FIG. 15 or the unequal set doses of the first medicament (1aa) and second medicament (11aa) as shown in FIG. 4 after the unlock of the user operable variable locking mechanisms (8,88) may be explained as follows.

Referring FIG. 3, FIG. 9, FIG. 10 and FIG. 15 on activation of the single activation button (6) for the chosen equal set doses of the first medicament (1aa) and second medicament (11aa) by the user, the single dispensing interface (7) may cause to rotate the dose drum (3) and dose drum (33); this may cause the dose delivery mechanism (5) shown in FIG. 16 and dose delivery mechanism (55) not shown in figure located in the housing (100), operably connected to the dose setting mechanisms (2,22), pushing out 12 IU medicament (1aa) and medicament (11aa) simultaneously via a common needle hub (7a) through a needle (7aa); the knob protrusion (8aa) and knob protrusion (88aa) aligned with the helical groove (3a) and helical groove (33a) respectively may travel in the helical groove guided path in the anti clockwise direction till the entire doses of medicaments (1aa,11aa) may be delivered. When this happens the knob protrusion (8aa) and knob protrusion (88aa) of the first medicament (1aa) and second medicament (11aa) may be at the junction i.e. the beginning of the proximal portion of the helical groove (3a) and helical groove (33a) and the proximal end of the longitudinal groove (3b) and longitudinal groove (33b). At this moment the relaxation of the spring (8b) and (88b) and their forces may result in the knob protrusion (8aa) and knob protrusion (88aa) going back to initial position of the longitudinal groove (3b) and longitudinal groove (33b) and the locking action may be completed.

As shown in FIG. 4 the first medicine (1aa) may be set at 8 IU and the second medicament (11aa) dose at 12IU; Referring FIG. 4 on activation of the single activation button (6) for the chosen unequal set doses of the first medicament (1aa) and second medicament (11aa) by the user, the single dispensing interface (7) may cause to rotate the dose drum (33) in the anti clock wise direction or clock wise direction depending on the inward helical groove or outward helical groove are provided on the dose drums (3,33); the dose delivery mechanism (5) shown in FIG. 16 and dose delivery mechanism (55) (not shown in figure) of the first medicament (1aa) and second medicament (11aa), operably connected to the dose setting mechanism (2) and dose setting mechanism (22) may push 4U medicament (11aa) from the cartridge (11a) only to start with via a common needle hub (7a) through a needle (7aa); Only the knob protrusion (88aa) may travel in the helical groove guided path in the anti clockwise direction till its dose indicator (99) may show 8 IU. When this may happen the dose indicator (99) may indicate 8 IU and the dose indicator (9) 8 IU, the chosen dose but none delivered. Continuing the activation of single activation button (6) the knob protrusion (8aa) and knob protrusion (88aa) may align with the helical groove (3a) and helical groove (33a) respectively and may travel in the helical groove guided path in the anti clockwise direction till the 8 IU doses of medicaments (1aa,11aa) be delivered through the needle (7aa). When this happens the knob protrusion (8aa) and knob protrusion (88aa) of the first medicament (1aa) and second medicament (11aa) may be at the junction i.e. the beginning of the proximal portion of the helical groove (3a) and helical groove (33a) and the proximal end of the longitudinal groove (3b) and longitudinal groove (33b). At this moment the relaxation of the spring (8b) and (88b) and their forces may result in the knob protrusion (8aa) and knob protrusion (88aa) going back to initial position of the longitudinal groove (3b) and longitudinal groove (33b) and the locking action may be completed.

As shown in FIG. 13 administration/delivery of the only medicament (11aa) may be explained as follows. Referring FIG. 13 may be an embodiment of the drug delivery device (12) of the invention wherein on activation of the single activation button (6) for a chosen variable dose of medicament (11aa) of 12 IU selected by unlocking the user operable variable dose locking mechanism (88) while the medicament (1aa) may be locked, the single dispensing interface (7) operably connected to the dose setting mechanism (22) may cause to rotate the dose drum dose drum (33) in the anti clock wise direction; the dose delivery mechanism (55) located in the housing (100) not shown in the figure, operably connected to the dose setting mechanism (22) may push 12 IU of medicine (11aa) from the cartridge (11a) via a common needle hub (7a) through a needle (7aa); When this happens knob protrusion (88aa) of the second medicament (11aa) may be at the junction i.e. the beginning of the proximal portion of the helical groove (33a) and the proximal end of the longitudinal groove (33b). At this moment the relaxation of the spring (88b) and its force may result in the knob protrusion (88aa) going back to initial position of the longitudinal groove (33b) and the locking action may be completed.

Similarly analogous to FIG. 13 (Figure not shown) there may be an embodiment of the drug delivery device (12) of the invention wherein on activation of the single activation button (6) for a chosen variable dose of medicament (1aa) of 12 IU selected by unlocking the user operable variable dose locking mechanism (8) while the medicament (11aa) may be locked, the single dispensing interface (7) operably connected to the dose setting mechanism (2) may cause to rotate the dose drum (3) in the anti clockwise direction; the dose delivery mechanism (5) shown in FIG. 16, operably connected to the dose setting mechanism (2) may push 12 IU of medicine (1aa) from the cartridge (11a) via a common needle hub (7a) through a needle (7aa); When this happens knob protrusion (8aa) of the first medicament (11aa) may be at the junction i.e. the beginning of the proximal portion of the helical groove (3a) and the proximal end of the longitudinal groove (3b). At this moment the relaxation of the spring (8b) and its force may result in the knob protrusion (8aa) going back to initial position of the longitudinal groove (3b) and the locking action may be completed.

The detailed description of a drug delivery device (12) in an embodiment of the invention for delivery of three medicaments, medicament (1aa), medicament (11aa) and optionally medicament (111*aa*) comprising user operable variable dose locking mechanism (8), user operable variable dose locking mechanism (88) and optionally user operable fixed dose locking mechanism (888) may be described as follows referring to FIG. 18 to FIG. 19. The drug delivery device (12) of the invention for delivery of three independently user selectable variable/fixed multiple doses of medicament (1*aa*) and medicament (11*aa*), may be contained in cartridge (1*a*) and cartridge (11*a*), of the medicament reservoir (1) and medicament reservoir (11); optionally, fixed dose of medicament (111*aa*) may be contained in cartridge (111*a*) of the medicament reservoir (111); a user operable variable dose locking mechanism (8) associated with medicament (1*aa*), a user operable variable dose locking mechanism (88) associated with medicament (11*aa*) may be mounted on the housing (10) and housing (100) and optionally a user operable fixed dose locking mechanism (888) may be mounted on the housing (1000) within a single device operatively connected to a single dispense interface (7); the device may comprise a dose setter (4), a dose drum (3) of the dose setting mechanism (2) contained within the housing (10); a dose setter (44), a dose drum (33) of the dose setting mechanism (22) contained within the housing (100); optionally a dose drum (333) of the dose setting mechanism (222) contained within the housing (1000); the device further may comprise a dose delivery mechanism (5) operably connected to the dose setting mechanism (2), a dose delivery mechanism (55) operably connected to the dose setting mechanism (22); and optionally a dose delivery mechanism (555) operably connected to the dose setting mechanism (222) (not shown in the FIG. 18); wherein the user operable variable dose locking mechanism (8) mounted on the housing (10) may be operably connected to the dose setter (4); the user operable variable dose locking mechanism (88) mounted on the housing (100) may be operably connected to the dose setter (44); and optionally the user operable fixed dose locking mechanism (888) mounted on the housing (1000) may be operably connected to the dose setter (444) which allow the selection of the appropriate doses of medicament (1*aa*) on unlocking the user operable variable dose locking mechanism (8), selection of the appropriate doses of medicament (11*aa*) on unlocking the user operable variable dose locking mechanism (88); and optionally selection of the appropriate doses of medicament (111*aa*) on unlocking the user operable fixed dose locking mechanism (888); activation of single activation button (6) by the user may dispense the selected doses of medicament (1*aa*), medicament (11*aa*) and medicament (111*aa*); and on completion of dispensation of doses user operable variable dose locking mechanism (8), user operable variable dose locking mechanism (88) and user operable fixed dose locking mechanism (888) may automatically get locked. The medicament (1*aa*), medicament (11*aa*) and medicament (111*aa*) may be delivered through a needle (7*aa*) attached to a common needle hub (7*a*). The needle hub (7*a*) may operably be connected to the medicament reservoir (1), medicament reservoir (11) and medicament reservoir (111).

Figure 18:
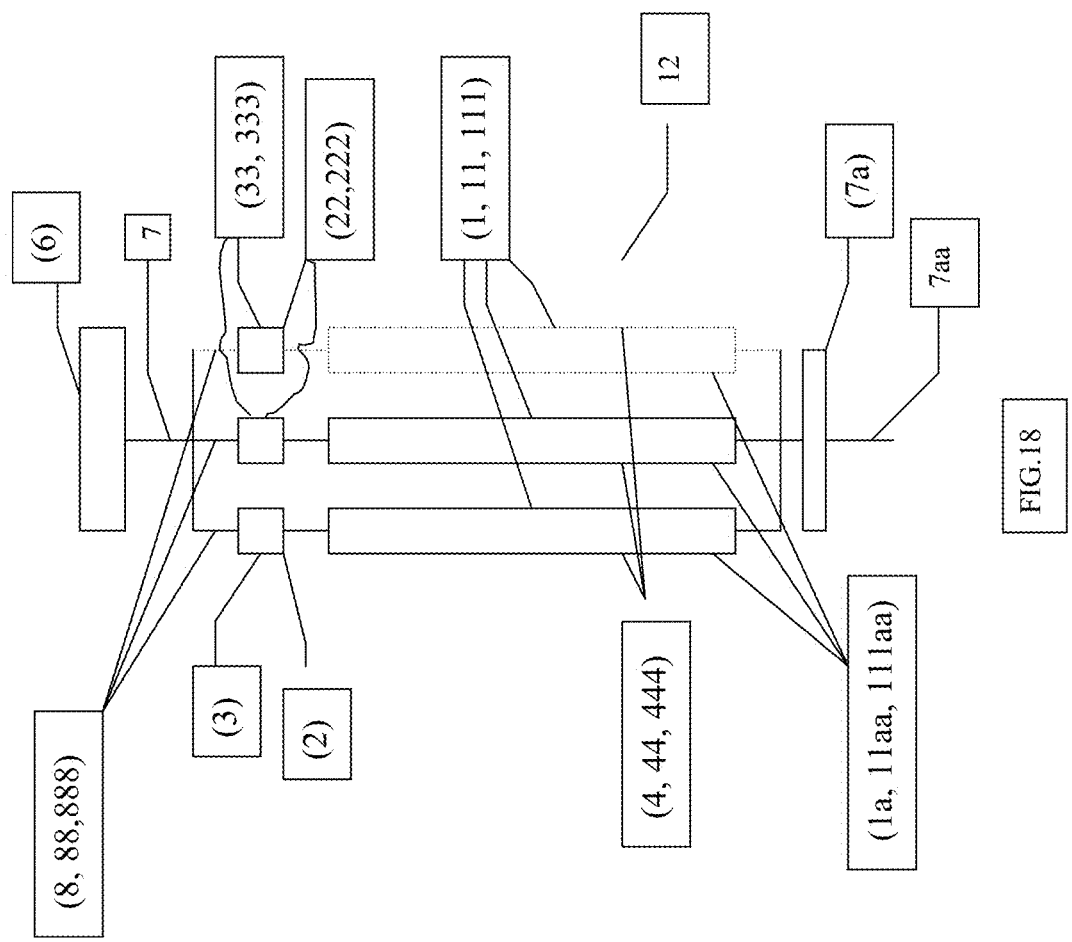
FIG. 18—Perspective view of locking mechanism linked with two variable dose setters and one fixed dose setter in lock condition in a drug delivery device (12) for delivery of first medicament (1aa), second medicament (11aa) and third medicament (111aa) by a single activation through a single interface.
Figure 19:
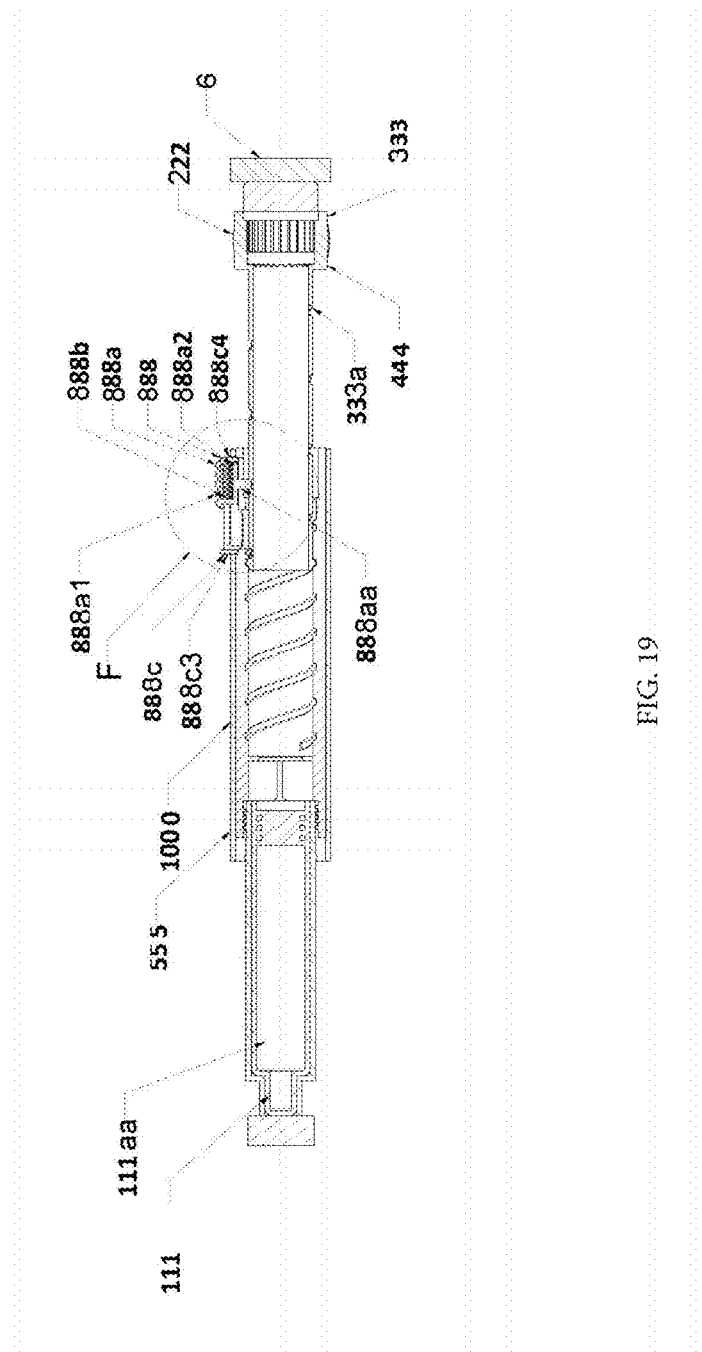
FIG. 19—A sectional view analogous to FIG. 16 for medicament (1aa) shown for fixed dose medicament ((111aa) of FIG. 18 showing the sliding knob of fixed dose setter in unlock condition for delivery of medicament (111aa) by a single activation through a single interface.

Referring to FIG. 18 and FIG. 19 the user operable fixed dose locking mechanism (888) of the third medicament (111*aa*) contained in the cartridge (111*a*) of the medicament reservoir (111) of the drug delivery device (12) may comprise a knob (888*a*), a spring (888*b*) and a bracket (888*c*). The bracket (888*c*) of the locking mechanism (888) of the third medicament (111*aa*) contained in the cartridge (111*a*) of the medicament reservoir (111) may be mounted on the outer surface of the housing (1000) firmly towards its proximal portion. The bracket (888*c*) may be held firmly on the outer surface of the housing (1000) by welding/integral moulding/snap fitting. The bracket (888*c*) may be of any shape such as rectangular, square, trapezoidal, oval etc. In the embodiment of the invention as shown in FIG. 19 the bracket (888*c*) may be of rectangular shape. The bracket (888*c*) may be bound by bracket longitudinal surfaces (888*c*1, 888*c*2) (not shown in figure) and bracket transverse (888*c*3, 888*c*4) surfaces which may be parallel to one another forming a rectangular shape within which the knob (888*a*) and spring (888*b*) may be located. The shape of the bracket (888*c*) may be same as that of bracket (8*c*) and bracket (88*c*). The spring (888*b*) may be of rectangular shape. Helical shaped spring (not shown in figure) may also be used and which may do the same function as that of rectangular shaped spring. The function of the spring (888*b*) may be to achieve the automatic locking of dose setter (444) after the delivery of the fixed dose and the counter level of the dose drum (333) may reach zero position. The material property of the spring (888*b*) may be such that it may withstand repeated compression and relaxation during the use of the device. The proximal portion of the relaxed spring (888*b*) may be colored red. The knob upper surface (8*a*1) may be colored green. The distal portion of the spring (888*b*) may be held in place between the knob upper surface (888*a*1) and knob lower surface (888*a*2) and proximal portion of the spring (888*b*) may be held by bias with the proximal portion of the bracket transverse surface (888*c*4).

Referring to FIG. 19 the knob (888*a*) may be bounded by knob upper surface (888*a*1) at the top, knob lower surface (888*a*2) at the bottom, knob vertical surface (888*a*3) at its side towards its distal end; a knob protrusion (888*aa*) may project downwardly closer to the middle portion of the knob lower surface (888*a*2). The knob (888*a*) may be arrested within the bracket (888*c*). The knob (888*a*) may be located towards the distal end of the bracket (888*c*) as shown in FIG. 19. The intention of placement of the knob (888*a*) within the bracket (888*c*) may be that the knob (888*a*) should not come off during its usage. The knob (888*a*) may be the key component which establish contact with the dose drum (333) of the dose setting mechanism (222) of the drug delivery device (12) by mating of the knob protrusion (888*aa*) with the longitudinal groove (333*b*) or inward helical groove (333*a*) of the dose drum (333) during the locking or unlocking of the user operable fixed dose locking mechanism (888).

Referring to FIG. 18 the user operable fixed dose locking mechanism (888) of the drug delivery device (12) with the third medicament (111*aa*) inside the cartridge (111*a*) in its start position would be in the locked condition. The technical features for the locking of the third medicament (111*aa*) may also be the same as that for the first medicament (1*aa*) and second medicament (11*aa*) and the same may be understood by referring FIG. 2 and FIG. 5 to FIG. 8. In the lock condition the knob vertical surface (888*a*3) may bias the proximal end of the distal bracket transverse surface (888*c*3) by the distal end relaxation force of the spring (888*b*); further proximal end of the relaxed spring (888*b*) may mate with distal end of proximal bracket transverse surface (888*c*4); knob (888*a*) may be held in place due to this mating of the knob vertical surface (888*a*3) with distal bracket transverse surface (888*c*3) by the distal end relaxation force of the spring (888*b*) and the mating of proximal end of the relaxed spring (888*b*) with the distal end of proximal bracket transverse surface (888*c*4). And when this happens the knob protrusion (888*aa*), so located on the knob lower surface (888*a*2), may align with the proximal portion of the longitudinal groove (333*b*) of the dose drum (333).

However the chosen dose setting (222) and dispensing mechanism (555) located in the housing (111) of the drug delivery device (12) for the delivery of third medicament (111aa) contained in the cartridge (111a) of the medicament reservoir (111) would be such that rotation of the dose setter (444) of the user operable fixed dose locking mechanism (888) by the user would set only fixed doses. For example for the chosen design of the dose setting (222) and dispensing mechanism (555) located in the housing (111) of the drug delivery device (12) for the delivery of 5 IU third medicament (111aa), the user would be able to set exactly 5 IU neither more nor less. In such a scenario unlocking the user operable fixed dose locking mechanism (888) and setting the dose of the drug delivery device (12) shown in FIG. 18 would deliver only 5 IU of third medicament (111aa) whatever may be the combination of chosen variable doses of the first medicament (1aa) and second medicament (11aa). Suppose if any other fixed dose such as 10 IU other than 5 IU of the third medicament (111aa) may have to delivered then the chosen dose setting (222) and dispensing mechanism (555) located in the housing (111) of the drug delivery device (12) for the delivery of third medicament (111aa) contained in the cartridge (111a) of the medicament reservoir (111) would be such that rotation of the dose setter (444) of the user operable fixed dose locking mechanism (888) by the user after its unlock would set only 10 IU fixed doses.

Unlocking the user operable fixed dose locking mechanism (888) may be described by referring to FIG. 18 and FIG. 19. Suppose a selected dose of the third medicament (111aa) may have to be administered, then the user operable fixed dose locking mechanism (888) of the drug delivery device (12) would have to be unlocked to set the desired dose. To set a dose, the knob (888a) of the locking mechanism (888) may to have to be slided or pushed towards the proximal portion of the drug delivery device (12). By doing so, the knob protrusion (888aa) of the knob (888a) may travel along longitudinal groove (333b) of the dose drum (333) in the proximal direction from its initial locked position. This movement may push the knob (888a) towards the proximal portion compressing the flexible spring (888b). This may align the knob protrusion (888aa) with the initial position of the helical groove (333a) of the dose drum (333). The proximal end of the longitudinal groove (333b) and the initial position in proximal portion of the helical groove (333a) may be one and the same. The knob protrusion (888aa) may take the immediate next position of the helical groove (333a) at the junction of the longitudinal groove (333b) and the proximal portion helical groove (333a) to support the compression force of the spring (888b). Further in the unlock condition the knob (888a) may be held in place in the bracket (888c) by the mating of the proximal portion or proximal end of the knob vertical surface (888a3) with the distal end of the spring (888b) in a compressed condition and the mating of the proximal end of the spring (888b) with the distal portion of the proximal bracket transverse surface (888c4). In the embodiment shown in FIG. 19 the fixed dose of the medicament (111aa) may be set at 5 IU. Referring to FIG. 19 it may be seen the knob protrusion (888aa) of the locking mechanism (888) may have travelled the path of the helical groove (333a) corresponding to the fixed dosage of the medicine (111aa). During fixed dosage setting the spring (888b) of the locking mechanism (888) would be in the compressed state as shown in FIG. 19.

The provision of user operable variable dose locking mechanism (8), user operable variable dose locking mechanism (88) and user operable fixed dose locking mechanism (888) in an embodiment of the drug delivery device (12) as shown in FIG. 18 for the delivery of variable doses of medicament (1aa), variable doses of medicament (11aa) and fixed dose of medicament (111aa) may allow the following flexibility of administration of the medicaments (1aa, 11aa, 111aa). The functioning of the user operable variable locking mechanism (8, 88) and delivery of the selected doses of the medicament (1aa) and medicament (11aa) in the embodiment of the drug delivery device (12) shown in FIG. 18 for delivery of three medicaments may be the same as shown in FIG. 1 to FIG. 17. Hence the references to FIG. 1 to FIG. 17 have been made to explain the delivery of medicament (1aa) and medicament (11aa) in the various embodiments of the drug delivery device (12) for delivery of three medicaments.

Referring FIG. 18 activation of the single activation button (6) for the chosen equal set doses of 12 IU of the first medicament (1aa) and second medicament (11aa) (analogous to FIG. 3) by the user after the unlocking of the user operable variable dose locking mechanisms (8,88) wherein the user operable fixed dose locking mechanism (888) may be locked, the single dispensing interface (7) may cause to rotate the dose drum (3) and dose drum (33); this may cause the dose delivery mechanism (5) (analogous to FIG. 16) and dose delivery mechanism (55) (not shown in figure) located in the housing (100), operably connected to the dose setting mechanisms (2,22), pushing out 12 IU medicament (1aa) and medicament (11aa) simultaneously via a common needle hub (7a) through a needle (7aa); the knob protrusion (8aa) and knob protrusion (88aa) aligned with the helical groove (3a) and helical groove (33a) respectively may travel in the helical groove guided path in the anti clockwise direction till the entire doses of medicaments (1aa,11aa) may be delivered. When this happens the knob protrusion (8aa) and knob protrusion (88aa) of the first medicament (1aa) and second medicament (11aa) may be at the junction i.e. the beginning of the proximal portion of the helical groove (3a) and helical groove (33a) and the proximal end of the longitudinal groove (3b) and longitudinal groove (33b). At this moment the relaxation of the spring (8b) and (88b) and their forces may result in the knob protrusion (8aa) and knob protrusion (88aa) going back to initial position of the longitudinal groove (3b) and longitudinal groove (33b) and the locking action may be completed.

Analogous to FIG. 4, the medicine (1aa) may be set at 8 IU and medicament (11aa) dose at 12 IU in the embodiment of the drug delivery device (12) shown in FIG. 18 wherein the user operable fixed dose locking mechanism (888) may be locked; Referring FIG. 18 on activation of the single activation button (6) for the chosen unequal set doses of the first medicament (1aa) and second medicament (11aa) by the user by unlocking the user operable variable dose locking mechanisms (8,88), the single dispensing interface (7) may cause to rotate the dose drum (33) in the anti clock wise direction or clock wise direction depending on whether the inward helical grove or outward helical groove are provided the dose drums (3,33); the dose delivery mechanism (5) analogous to FIG. 16 and dose delivery mechanism (55) (not shown in figure) of the first medicament (1aa) and second medicament (11aa), operably connected to the dose setting mechanism (2) and dose setting mechanism (22) may push 4U medicament (11aa) from the cartridge (11a) only to start with via a common needle hub (7a) through a needle (7aa); Only the knob protrusion (88aa) may travel in the helical groove guided path in the anti clockwise direction till its dose indicator (99) may show 8 IU. When this may happen the dose indicator (99) may indicate 8 IU and the dose indicator (9) 8 IU, the chosen dose but none delivered. Continuing the activation of single activation button (6) the knob protrusion (8aa) and knob protrusion (88aa) may align with the helical groove (3a) and helical groove (33a) respectively and may travel in the helical groove guided path in the anti clockwise direction till the 8 IU doses of medicaments (1aa,11aa) be delivered through the needle (7aa). When this happens the knob protrusion (8aa) and knob protrusion (88aa) of the first medicament (1aa) and second medicament (11aa) may be at the junction i.e. the beginning of the proximal portion of the helical groove (3a) and helical groove (33a) and the proximal end of the longitudinal groove (3b) and longitudinal groove (33b). At this moment the relaxation of the spring (8b) and (88b) and their forces may result in the knob protrusion (8aa) and knob protrusion (88aa) going back to initial position of the longitudinal groove (3b) and longitudinal groove (33b) and the locking action may be completed.

Analogous to FIG. 13 the administration/delivery of the only medicament (11aa) in the embodiment of the drug delivery device (12) for delivery of three medicaments as shown in FIG. 18 wherein the user operable variable dose locking mechanism (8) and user operable fixed dose locking mechanism (888) may be locked may be explained as follows. Analogous to FIG. 13 may be an embodiment of the drug delivery device (12) of the invention as shown in FIG. 18 wherein on activation of the single activation button (6) for a chosen variable dose of medicament (11aa) of 12 IU selected by unlocking the user operable variable dose locking mechanism (88) while the medicament (1aa) and medicament (111aa) may be locked, the single dispensing interface (7) operably connected to the dose setting mechanism (22) may cause to rotate the dose drum dose drum (33) in the anti clock wise direction; the dose delivery mechanism (55) located in the housing (100) (not shown in the figure), operably connected to the dose setting mechanism (22) may push 12 IU of medicine (11aa) from the cartridge (11a) via a common needle hub (7a) through a needle (7aa); When this happens knob protrusion (88aa) of the second medicament (11aa) may be at the junction i.e. the beginning of the proximal portion of the helical groove (33a) and the proximal end of the longitudinal groove (33b). At this moment the relaxation of the spring (88b) and its force may result in the knob protrusion (88aa) going back to initial position of the longitudinal groove (33b) and the locking action may be completed.

Similarly analogous to FIG. 13 (Figure not shown) the administration/delivery of the only medicament (1aa) in the embodiment of the drug delivery device (12) of the invention for delivery of three medicaments as shown in FIG. 18 wherein the user operable variable dose locking mechanism (88) and user operable fixed dose locking mechanism (888) may be locked may be explained as follows. Analogous to FIG. 13 may be an embodiment of the drug delivery device (12) of the invention wherein on activation of the single activation button (6) for a chosen variable dose of medicament (1aa) of 12 IU selected by unlocking the user operable variable dose locking mechanism (8) while the medicament (11aa) and medicament (111aa) may be locked, the single dispensing interface (7) operably connected to the dose setting mechanism (2) may cause to rotate the dose drum (3) in the anti clockwise direction; the dose delivery mechanism (5) shown in FIG. 16, operably connected to the dose setting mechanism (2) may push 12 IU of medicine (1aa) from the cartridge (1a) via a common needle hub (7a) through a needle (7aa); When this happens knob protrusion (8aa) of the first medicament (1aa) may be at the junction i.e. the beginning of the proximal portion of the helical groove (3a) and the proximal end of the longitudinal groove (3b). At this moment the relaxation of the spring (8b) and its force may result in the knob protrusion (8aa) going back to initial position of the longitudinal groove (3b) and the locking action may be completed.

Similarly analogous to FIG. 13 (Figure not shown) the administration/delivery of the only medicament (111aa) in the embodiment of the drug delivery device (12) of the invention for delivery of three medicaments as shown in FIG. 18 and FIG. 19 wherein the user operable variable dose locking mechanism (8) and user operable variable dose locking mechanism (88) may be locked may be explained as follows. As shown in FIG. 19 may be an embodiment of the drug delivery device (12) of the invention wherein on activation of the single activation button (6) for the fixed dose of medicament (111aa) of 5 IU selected by unlocking the user operable fixed dose locking mechanism (888) while the medicament (1aa) and the medicament (11aa) may be locked, the single dispensing interface (7) operably connected to the dose setting mechanism (222) may cause to rotate the dose drum (333) in the anti clockwise direction; the dose delivery mechanism (555) shown in FIG. 19, operably connected to the dose setting mechanism (222) may push 5 IU of medicine (111aa) from the cartridge (111a) via a common needle hub (7a) through a needle (7aa); When this happens knob protrusion (888aa) of the third medicament (111aa) may be at the junction i.e. the beginning of the proximal portion of the helical groove (333a) and the proximal end of the longitudinal groove (333b). At this moment the relaxation of the spring (888b) and its force may result in the knob protrusion (888aa) going back to initial position of the longitudinal groove (333b) and the locking action may be completed.

Similarly analogous to FIG. 3, FIG. 9, FIG. 10 and FIG. 15 (Similar figures not shown for three medicament embodiments) the administration/delivery of medicament (1aa) and medicament (111aa) in the embodiment of the drug delivery device (12) of the invention for delivery of three medicaments as shown in FIG. 18 and FIG. 19 wherein the user operable variable dose locking mechanism (88) may be locked may be explained as follows. Analogous to FIG. 3, FIG. 9, FIG. 10 and FIG. 15 may be an embodiment of the drug delivery device (12) of the invention wherein on activation of the single activation button (6) for the chosen variable set doses of the first medicament (1aa) and the fixed dose of the third medicament (111aa) by the user, the single dispensing interface (7) may cause to rotate the dose drum (3) and dose drum (333); this may cause the dose delivery mechanism (5) analogous to as shown in FIG. 16 and dose delivery mechanism (555) shown in FIG. 19 located in the housing (1000), operably connected to the dose setting mechanisms (2,222), pushing out the chosen doses of the first medicament (1aa) and third medicament (11aa) via a common needle hub (7a) through a needle (7aa); the knob protrusion (8aa) and knob protrusion (888aa) aligned with the helical groove (3a) and helical groove (333a) respectively may travel in the helical groove guided path in the anti clockwise direction till the entire doses of first medicament and third medicament (1aa,111aa) may be delivered. When this happens the knob protrusion (8aa) and knob protrusion (888aa) of the first medicament (1aa) and third medicament (111aa) may be at the junction i.e. the beginning of the proximal portion of the helical groove (3a) and helical groove (333a) and the proximal end of the longitudinal groove (3b) and longitudinal groove (333b). At this moment the relaxation of the spring (8b) and (888b) and their forces may result in the knob protrusion (8aa) and knob protrusion (888aa) going back to initial position of the longitudinal groove (3b) and longitudinal groove (333b) and the locking action may be completed. In the embodiment of this invention, if the first medicament (1aa) dose and third medicament (111aa) fixed dose are equal (e.g. 5 IU), then the medicament (1aa) and medicament (111aa) may be simultaneously delivered. If the variable first medicament (1aa) dose set may be lower e.g. 3 IU) than the fixed dose (111aa) (e.g. 5 IU), then the then the higher dose of the fixed dose may be delivered first alone till both the doses may be equal (2 IU), and subsequently both the medicament (1aa) and medicament (111aa) may be delivered simultaneously. Similarly, If the variable first medicament (1aa) dose set (e.g. 10 IU) may be higher than the fixed dose (111aa) (e.g. 5 IU), then the higher dose of the medicament (1aa) (5 IU) may be delivered first alone till both the doses may be equal, and subsequently both the medicament (1aa) and fixed dose medicament (111aa) may be delivered simultaneously.

Analogous to figures FIG. 3, FIG. 9, FIG. 10 and FIG. 15 may be an embodiment of the drug delivery device (12) for delivery of three medicaments (1aa, 11aa, 111aa) where in on activation of the single activation button (6) for the chosen equal set doses of the first medicament (1aa) and third medicament (111aa) by the user while the medicament (11aa) may be locked, the single dispensing interface (7) may cause to rotate the dose drum (3) and dose drum (333); this may cause analogous to the the dose delivery mechanism (5) shown in FIG. 16 and dose delivery mechanism (555) shown in FIG. 19 located in the housing (1000), operably connected to the dose setting mechanisms (2,222), pushing out 5 IU medicament (1aa) and medicament (111aa) simultaneously via a common needle hub (7a) through a needle (7aa); the knob protrusion (8aa) and knob protrusion (888aa) aligned with the helical groove (3a) and helical groove (333a) respectively may travel in the helical groove guided path in the anti clockwise direction till the entire doses of medicaments (1aa,111aa) may be delivered. When this happens the knob protrusion (8aa) and knob protrusion (888aa) of the first medicament (1aa) and second medicament (111aa) may be at the junction i.e. the beginning of the proximal portion of the helical groove (3a) and helical groove (333a) and the proximal end of the longitudinal groove (3b) and longitudinal groove (333b). At this moment the relaxation of the spring (8b) and (888b) and their forces may result in the knob protrusion (8aa) and knob protrusion (888aa) going back to initial position of the longitudinal groove (3b) and longitudinal groove (333b) and the locking action may be completed.

As shown in FIG. 18 the drug delivery device (12) of the invention for delivery of three medicaments may be used for the administration/delivery of three medicaments medicament (1aa), medicament (11aa) and medicament (111aaa). In an embodiment (Figure not shown) the first medicine (1aa) may be set at 2 IU, the second medicament (11aa) may be set at 3 IU and the third medicament (111aa) dose at 5 IU; On activation of the single activation button (6) for the chosen unequal set doses of the first medicament (1aa), second medicament (11aa) and the fixed dose of the third medicament (111aa) by the user, the single dispensing interface (7) may cause to rotate the dose drum (333) in the anti clock wise direction; the dose delivery mechanism (555) shown in FIG. 19, the dose delivery mechanism (5) (shown in FIG. 16) and the dose delivery mechanism (55) (not shown in figure), operably connected to the dose setting mechanism (222), the dose setting mechanism (22) and the dose setting mechanism (2) may push 2U medicaments of (111aa) only from the cartridge (111a) to start with via a common needle hub (7a) through a needle (7aa); Only the knob protrusion (888aa) may travel in the helical groove guided path in the anti clockwise direction till its dose indicator (999) may show 3 IU. When this may happen the dose indicator (999) may indicate 3 IU and the dose indicator (99) 3 IU, the chosen dose but none delivered. Continuing the activation of single activation button (6) the knob protrusion (888aa) and knob protrusion (88aa) may align with the helical groove (333a) and helical groove (33a) respectively and may travel in the helical groove guided path in the anti clockwise direction till the 1 IU doses of medicaments (11aa,111aa) be delivered through the needle (7aa). When this may happen the dose indicator (999) may indicate 2 IU and the dose indicator (99) 2 IU, and the dose indicator (9) 2 IU, the chosen dose but none delivered. Continuing the activation of single activation button (6) the knob protrusion (888aa), knob protrusion (88aa) and knob protrusion (8aa) may align with the helical groove (333a), helical groove (33a) and helical groove (3a) respectively and may travel in the helical groove guided path in the anti clockwise direction till the 2 IU doses of medicaments (1aa,11aa,111aa) may be delivered simultaneously through the needle (7aa). When this happens the knob protrusion (8aa), knob protrusion (88aa) and knob protrusion (888aa) of the first medicament (1aa), second medicament (11aa) and third medicament (111aa) may be at the junction i.e. the beginning of the proximal portion of the helical groove (3a), helical groove (33a) and helical groove (333a) and the proximal end of the longitudinal groove (3b), longitudinal groove (33b) and longitudinal groove (333b). At this moment the relaxation of the spring (8b), spring (88b) and spring (888b) and their forces may result in the knob protrusion (8aa), knob protrusion (88aa) and knob protrusion (888aa) going back to initial position of the longitudinal groove (3b), longitudinal groove (33b) and longitudinal groove (333b) and the locking action may be completed.

A summary of nomenclature of the components used in the instant invention are given in the table below. In the below table like numerals of the components correspond to the first medicament (1aa), second medicament (11aa) and third medicament (111aa) in the medicament reservoir (1), medicament reservoir (11) and medicament reservoir (111) respectively;

TABLE

| Sl no | Component Number | Description |
| --- | --- | --- |
| 1 | 1, 11, 111 | Medicament reservoir |
| 2 | 1a, 11a, 111a | Cartridge |
| 3 | 1aa, 11aa, 111aa | Medicament |
| 4 | 2, 22, 222 | Dose setting mechanism |
| 5 | 3, 33, 333 | Dose drum |
| 6 | 3a, 33a, 333a | Dose drum helical groove |
| 7 | 3b, 33b, 333b | Dose drum longitudinal groove |
| 8 | 4, 44, 444 | Dose setter |
| 9 | 5, 55, 555 | Dose delivery mechanism |
| 10 | 6 | Single activation button |
| 11 | 7 | Single dispensing interface |
| 12 | 7a | Needle hub |
| 13 | 7aa | needle |
| 14 | 8, 88 | User operable variable dose locking mechanism |
| 15 | 888 | User operable fixed dose locking mechanism |
| 16 | 8a, 88a, 888a | knob |
| 17 | 8a1, 88a1, 888a1 | Knob upper surface |
| 18 | 8a2, 88a2, 888a2 | Knob lower surface |

TABLE-continued

| Sl no | Component Number | Description |
|---|---|---|
| 19 | 8a3, 88a3, 888a3 | Knob vertical surface |
| 20 | 8aa, 88aa, 888aa | Knob protrusion |
| 21 | 8b, 88b, 888b | Spring |
| 22 | 8c, 88c, 888c | bracket |
| 23 | 8c1, 8c2, 88c1, 88c2, 888c1, 888c2 | Bracket longitudinal surfaces |
| 24 | 8c3, 8c4, 88c3, 88c4, 888c3, 888c4 | Bracket transverse surfaces |
| 25 | 9, 99, 999 | Dose Indicator |
| 26 | 10, 100, 1000 | Housing |
| 27 | 12 | Drug delivery device |
| 28 | 13 | Container |
| 29 | 14 | Cover |

We claim:

1. A drug delivery device capable of delivering two or more medicaments, at least one of which may be delivered in a variable dose, said device comprising:
   (A) two or more housings;
   (B) a common needle hub;
   (C) a dispensing interface;
   (D) an activation mechanism; and
   (E) a user operable variable dose locking mechanism,
wherein:
   (I) each of said housings comprises:
      (a) a dose setting mechanism;
      (b) a dose delivery mechanism; and
      (c) a removable medicament cartridge,
wherein said dose setting mechanism comprises:
      (i) a dose setter and
      (ii) a dose drum comprising:
         a helical groove on an outer surface thereof and
         a longitudinal groove, and
   (II) said user operable variable dose locking mechanism is capable of locking and unlocking the dose setting mechanism and the dose delivery mechanism, and wherein said locking mechanism comprises:
      (a) a knob;
      (b) a spring having a proximal end and a distal end; and
      (c) a bracket having a proximal end and a distal end, mounted on the housing,
wherein said knob is located towards the distal end of said bracket, and wherein the knob comprises:
      (i) an upper surface;
      (ii) a lower surface;
      (iii) a vertical surface; and
      (iv) a protrusion located in a middle portion of said lower surface,
wherein the knob protrusion is selectively capable of alignment with the longitudinal groove of the dose drum and the helical groove of the dose drum; and wherein the knob protrusion can be slid in a proximal direction from alignment with the longitudinal groove of the dose drum and into alignment with the helical groove of the dose drum in order to move the dose setter from a locked to an unlocked condition, respectively.

2. The drug delivery device according to claim 1 wherein the dose drum longitudinal groove is provided on an outer surface of the dose drum towards a proximal portion of the dose drum and extends distally and terminates immediately before the helical groove of the dose drum.

3. The drug delivery device of claim 1 wherein the bracket comprises longitudinal surfaces and transverse surfaces, and: (1) the longitudinal surfaces run parallel to one another from a proximal end to the distal end of the bracket; (2) one of the transverse surfaces is towards a distal end of the bracket, and the other transverse surface is towards the proximal end of the bracket.

4. The drug delivery device of claim 3 wherein the knob vertical surface biases the distal bracket transverse surface when the dose setting mechanism is locked.

5. The drug delivery device of claim 4 wherein the knob is held in place in the bracket by the mating of the knob vertical surface with the bracket transverse surface which is positioned towards the distal end of the bracket when the dose setting mechanism is locked.

6. The drug delivery device of claim 3 wherein the proximal end of the spring in a relaxed condition biases the bracket transverse surface which is positioned towards the proximal end of the bracket, and the distal end of the spring biases the bracket transverse surface which is positioned towards the distal end of the bracket when the dose setting mechanism is locked.

7. The drug delivery device of claim 3 wherein the proximal end of the spring in a compressed condition biases the bracket transverse surface which is positioned towards the proximal end of the bracket, and the distal end of the spring biases the bracket transverse surface which is positioned towards the distal end of the bracket when the dose setting mechanism is unlocked.

8. The drug delivery device of claim 1 wherein the knob vertical surface biases the distal end of the spring when the dose setting mechanism is unlocked.

9. The drug delivery device of claim 8 wherein the knob is held in place in the bracket by the mating of the knob vertical surface with the distal end of the spring in a compressed condition when the dose setting mechanism is unlocked.

* * * * *